(12) United States Patent
Allen et al.

(10) Patent No.: US 9,147,273 B1
(45) Date of Patent: Sep. 29, 2015

(54) SYSTEM AND METHOD FOR MODELING AND ANALYZING DATA VIA HIERARCHICAL RANDOM GRAPHS

(75) Inventors: David L. Allen, Thousand Oaks, CA (US); Tsai-Ching Lu, Wynnewood, PA (US); David J. Huber, Venice, CA (US); Hankyu Moon, Aguora Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 921 days.

(21) Appl. No.: 13/029,073

(22) Filed: Feb. 16, 2011

(51) Int. Cl.
*G06T 11/20* (2006.01)
*G06F 19/26* (2011.01)

(52) U.S. Cl.
CPC .............. *G06T 11/206* (2013.01); *G06F 19/26* (2013.01)

(58) Field of Classification Search
CPC ....... G06T 11/20; G06T 11/206; G06F 19/24; G06F 19/26; G06F 17/3053; G06F 21/56; G06Q 10/00; Y10S 707/93; Y10S 707/937; Y10S 707/959; H04L 63/145; H04L 63/1416; H04L 63/1425
USPC .................. 345/440; 707/737–740, 749, 803; 709/206
See application file for complete search history.

(56) References Cited

U.S. PATENT DOCUMENTS

| | | | |
|---|---|---|---|
| 2002/0161736 A1* | 10/2002 | Beygelzimer et al. | 707/1 |
| 2006/0271564 A1* | 11/2006 | Meng Muntz et al. | 707/100 |
| 2008/0228824 A1* | 9/2008 | Kenedy et al. | 707/104.1 |
| 2009/0037390 A1* | 2/2009 | Handley | 707/3 |
| 2009/0153661 A1* | 6/2009 | Cheng et al. | 348/143 |
| 2010/0161369 A1* | 6/2010 | Farrell et al. | 705/8 |
| 2010/0174747 A1* | 7/2010 | Farrell et al. | 707/776 |
| 2011/0055379 A1* | 3/2011 | Lin et al. | 709/224 |
| 2011/0097001 A1* | 4/2011 | Labbi et al. | 382/225 |
| 2011/0283361 A1* | 11/2011 | Perdisci et al. | 726/24 |
| 2013/0254305 A1* | 9/2013 | Cheng et al. | 709/206 |

OTHER PUBLICATIONS

Tomasz Tylenda, Ralitsa Angelova, Srikanta Bedathur, Towards Time-aware Link Prediction in Evolving Social Networks, 2009, The 3rd SNA-KDD Workshop '09 (SNA-KDD'09), Paris, France.*
Jingfeng Guo, Hongwei Guo, Multi-features Link Prediction Based on Matrix 2010, International Conference on Computer Design and Appliations (ICCDA 2010), Qinhuangdao, China.*

(Continued)

*Primary Examiner* — Xiao Wu
*Assistant Examiner* — Michael J Cobb
(74) *Attorney, Agent, or Firm* — Christie, Parker & Hale, LLP

(57) ABSTRACT

The present invention is directed to a data processing apparatus and a computer implemented method for modeling and analyzing relational data represented in a network that includes a plurality of nodes and a plurality of connections between the nodes. The method includes assigning at least one weight to a connection between two nodes in the network. A set of possible dendrograms is then generated for the network, and a likelihood of each dendrogram in the set is determined. The determination of the likelihood is based on at least the one weight of the connection. One of the dendrograms from the set is selected as an optimal dendrogram based on the determined likelihood. The selected dendrogram is then output via an output device. The dendrogram may be used to predict missing links or identify any possible false-positive (noisy) links within a relational dataset.

18 Claims, 18 Drawing Sheets

(56) References Cited

OTHER PUBLICATIONS

Yongjin Park, Cristopher Moore, Joel S. Bader, Dynamic Networks from Hierarchical Bayesian Graph Clustering, 2010, PLoS One 5(1): e8118. doi:10.1371/journal.pone.0008118.*
Benjamin H. Good, Modularity and Community Detection in Complex Networks, 2010, Thesis, Swarthmore College, Swarthmore, PA.*
Mason A. Porter, Jukka-Pekka Onnela, Peter J. Mucha, Communities in Networks, 2009, Notices of the AMS, 56(9):1082-1097,1164-1166.*
Evrim Acar, Daniel M. Dunlavy, Tamara G. Kolda, Link Prediction on Evolving Data using Matrix and Tensor Factorizations, 2009, IEEE International Conference on Data Mining Workshops, Miami, FL, pp. 262-269.*
Jonathan W. Berry, Bruce Hendrickson, Randall A. LaViolette, Cynthia A. Phillips, Tolerating the Community Detection Resolution Limit with Edge Weighting 2009, Physics and Society, arXiv:0903. 1072v2 [physics.soc-ph].*
Angela Orebaugh, Greg Morris, Ethereal Packet Sniffing, 2004, Syngress, pp. 167-168, ISBN: 9781932266825.*
Stephen Prata, C++ Primer Plus, 6th Edition, 2011, Chapter 3: Dealing with Data, pp. 65-109, ISBN: 9780132781145.*
Stephen Prata, C++ Primer Plus, 3rd Edition, 1998, Chapter 3. Data and C, pp. 37-67, ISBN: 1571691618.*
VT2006, Lecture 3B: Floating Point 2006, Kth Royal Institute of Technology, Stockholm, Sweden, retrieved from <http://www.nada.kth.se/kurser/kth/2D1377/schema/f03B-floatingpoint.pdf> on Sep. 24, 2014.*
Jean-Pierre Barthélemy, F.R. McMorris, The Median Procedure for n-Trees, 1986, Journal of Classification, 3:329-334.*
Bryant, A Classification of Consensus Methods for Phylogenetics, (DIMACS Series in Discrete Mathematics and Theoretical Computer Science) 1991, 21 pages, School of Computer Science and Department of Mathematics and Statistics, McGill University, Montréal, Québec.
Clauset, et al., Hierarchical Structure and the Prediction of Missing Links in Networks, Nature, vol. 453, May 2008, pp. 98-101, Nature Publishing Group.
Clauset, et al., Hierarchical Structure and the Prediction of Missing Links in Networks, Supplementary Information, May 2008, 5 pages, www.nature.com/nature.
Newman, et al. Finding and Evaluating Community Structure in Networks, Physical Review E 69, 026113 (2004), 15 pages, The American Physical Society.
Palla, et al., Uncovering the Overlapping Community Structure of Complex Networks in Nature and Society, Nature, vol. 435/9, Jun. 2005/doi:10.1038/nature03607; pp. 814-818,Nature Publishing Group.
Clauset, et al., Structural Inference of Hierarchies in Networks, Proceedings of the 23rd International Conference on Machine Learning, Oct. 9, 2006, 8 pgs., Pittsburgh, PA.
Frey, et al., Clustering by Passing Messages Between Data Points, Science AAAS, vol. 315, Feb. 16, 2007, pp. 971-976, www.sciencemag.org.
Rosvall, et al., An Information-Theoretic Framework for Resolving Community Structure in Complex Networks, PNAS, May 1, 2007, pp. 7327-7331, vol. 104, No. 18, www.pnas.org/cgi/doi/10.1073.
Newman, et al., Mixture Models and Exploratory Analysis in Networks, PNAS, Jun. 5, 2007, pp. 9564-9569, vol. 104, No. 23, www.pnas.org/cgi/doi/10.1073.
Viswanathan, et al., Lévy Flights and Superdiffusion in the Context of Biological Encounters and Random Searches, ScienceDirect, Physics of Life Reviews 5 2008) pp. 133-150 Elsevier B.V., www.sciencedirect.com.
Kroonenberg, Applied Multiway Data Analysis, John Wiley & Sons, Inc., Publication, Hoboken, New Jersey, 2008, 19 pgs [553 pgs.].
González, et al., Understanding Individual Human Mobility Patterns, Nature, vol. 453, Jun. 5, 2008, pp. 779-782, Nature Publishing Group.

Kolda, et al., Tensor Decompositions and Applications, Siam Review, Jun. 10, 2008, pp. 1-47.
Hofman, et al., A Bayesian Approach to Network Modularity, Physics. data-an, Jun. 23, 2008, 4 pages, Columbia University, New York, N.Y.
Wang, et al., Understanding the Spreading Patterns of Mobile Phone Viruses, Science AAAS, vol. 324, May 22, 2009, pp. 1071-1076, Washington, D.C.
Halary, et al., Network Analyses Structure Genetic Diversity in Independent Genetic Worlds, PNAS, vol. 107, No. 1, Jan. 5, 2010, pp. 127-132.
Halary, et al., Supporting Information, 17 pages, www.pnas.org/cgi/content/short/10.1073/pnas.0908978107 Jan. 5, 2010.
Allen, David et al., Hierarchical Random Graphs for Networks with Weighted Edges and Multiple Edge Attributes, journal, Jul. 18-21, 2011, 7 pages, HRL Laboratories, LLC, Malibu, CA, USA.
Bhattacharya, I. et al., Collective Entity Resolution in Relational Data, article, Mar. 2007, 36 pages, vol. 1, No. 1, Article 5, ACM Transactions on Knowledge Discovery from Data, University of Maryland, College Park, USA.
Blei, David M. et al., Hierarchical Topic Models and the Nested Chinese Restaurant Process, journal, 2003, pp. 17-24, Morgan Kaufmann, San Mateo, CA, USA.
Bilgic, Mustafa et al., Active Interference for Collective Classification, journal, 2010, 4 pages, Association for the Advancement of Artificial Intelligence.
Brim, Sergey et al., The anatomy of a large-scale hypertextual Web search engine; journal, 1998, 11 pages, Elsevier Science B.V.
Clauset, Aaron et al., Hierarchial structure and the prediction of missing links in networks, journal, May 1, 2008, pp. 98-101, vol. 453, Nature Publishing Group.
Gamon, Michael et al., Pulse: Mining Customer Opinions from Free Text, journal, 2005, pp. 121-132, Springer-Verlag, Berlin Heidelberg.
González, Marta C. et al., Understanding individual human mobility patterns, article, and Addendum, 1 page, Jun. 5, 2008, pp. 779-782, vol. 453, Nature Publishing Group, Boston, Massachusetts, USA.
Hu, Minqing et al., Mining and Summarizing Customer Reviews, journal, Aug. 22-25, 2004; pp. 168-177, ACM, Seattle Washington, USA.
Iniguez, Gerardo et al., Opinion and community formation in coevolving networks, article, Nov. 4, 2009, 10 pages.
Jeh, Glen et al., SimRank: A Measure of Structural-Context Similarity, journal, 2002, pp. 538-543, ACM, Edmonton, Alberta, Canada.
Kapoor, Ashish et al., Breaking Boundaries: Active Information Acquisition Across Learning and Diagnosis, journal, 2009, 9 pages, Microsoft Research, Redmond Way, WA, USA.
Kim, Min-Soo et al., A Particle-and-DensityBased Evolutionary Clustering Method for Dynamic Networks, journal Aug. 24-28, 2009, pp. 622-633, VLDB Endowment, ACM, Lyon, France.
Leskovec, Jure et al., Signed Networks in Social Media, journal, Apr. 10-15, 2010, 10 pages, ACM, Atlanta, Georgia, USA.
Luxburg, Ulrike von, A tutorial on spectral clustering, journal, Aug. 22, 2007, 24 pages, Springer Science + Business Media, LLC.
Newman, M.E.J., Networks: Networks of Information, 2010, pp. 63-77, Ch. 4, Oxford University Press.
Newman, M.E.J., Networks: Matrix Algorithms and Graph Partitioning, 2010, pp. 345-392, Ch. 11, Oxford University Press.
Newman, M.E.J., Networks: Random Graphs, 2010, pp. 397-427, Ch. 12, Oxford University Press.
Pang, Bo et al., Opinion mining and settlement analysis, journal, 2008, 94 pages, vol. 2, No. 1-2, Foundations and Trends in Information Retrieval.
Pearl, Judea., Probabilistic Reasoning in Intelligent Systems: Networks of Plausible Inference, article, 1988, 49 pages, Ch. 4, Morgan Kaufmann, San Mateo, CA, USA.
Rattigan, Matthew J. et al., Exploiting network structure for active inference in collective classification, journal, 2007, 9 pages, Knowledge Discovery Laboratory, Department of Computer Science, University of Massachusetts, Amherst, USA.

(56) References Cited

OTHER PUBLICATIONS

Sun, Yizhou et al., RankClus: Integrating Clustering with Ranking for Heterogeneous Information Network Analysis, journal, Mar. 24-26, 2009, pp. 565-576, ACM, Saint Petersburg, Russia.

Sun, Yizhou et al., Ranking-Based Clustering of Heterogeneous Information Networks with Star Network Schema, journal, Jul. 28-Jul. 1, 2009, pp. 797-805, ACM, Paris France.

Vespignani, Alessandro, Predicting the Behavior of Techno-Social Systems, article, Jul. 24, 2009, 5 pages, vol. 325, Science AAAS, Washington, D.C., USA.

Wang, Chi et al., Mining Advisor-Advisee Relationships from Research Publication Networks, journal, Jul. 26-28, 2010, pp. 203-212, ACM, Washington, D.C., USA.

Yin, Xiaoxin et al., Object Distinction: Distinguishing Objects with Identical Names, journal, 2007, pp. 1242-1246, IEEE.

Yin, Xiaoxin et al., Truth Discovery with Multiple Conflicting Information Providers on the Web, journal, 2008, pp. 796-808, IEEE Computer Society.

Yu, Yintao et al., iNextCUbe: Information Network-Enhanced Text Cube, journal, Aug. 24-28, 2009, 4 pages, VLDB Endowment, ACM, Lyon, France.

Zhang, Duo et al., Topic Cube: Topic Modeling for OLAP on Multidimensional Text Databases, journal, Apr. 2009, pp. 1124-1135, in Proc. 2009 SIAM Int. Conf. on Data Mining, Sparks, NV, USA.

Zhuang, Li et al., Movie Review Mining and Summarization, journal, Nov. 5-11, 2006, pp, 43-49, ACM, Arlington, Virginia, USA.

\* cited by examiner

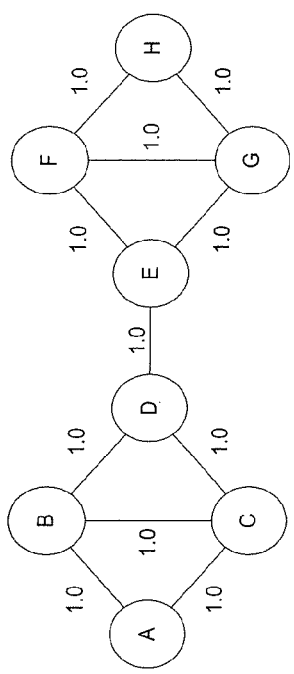
FIG. 6A
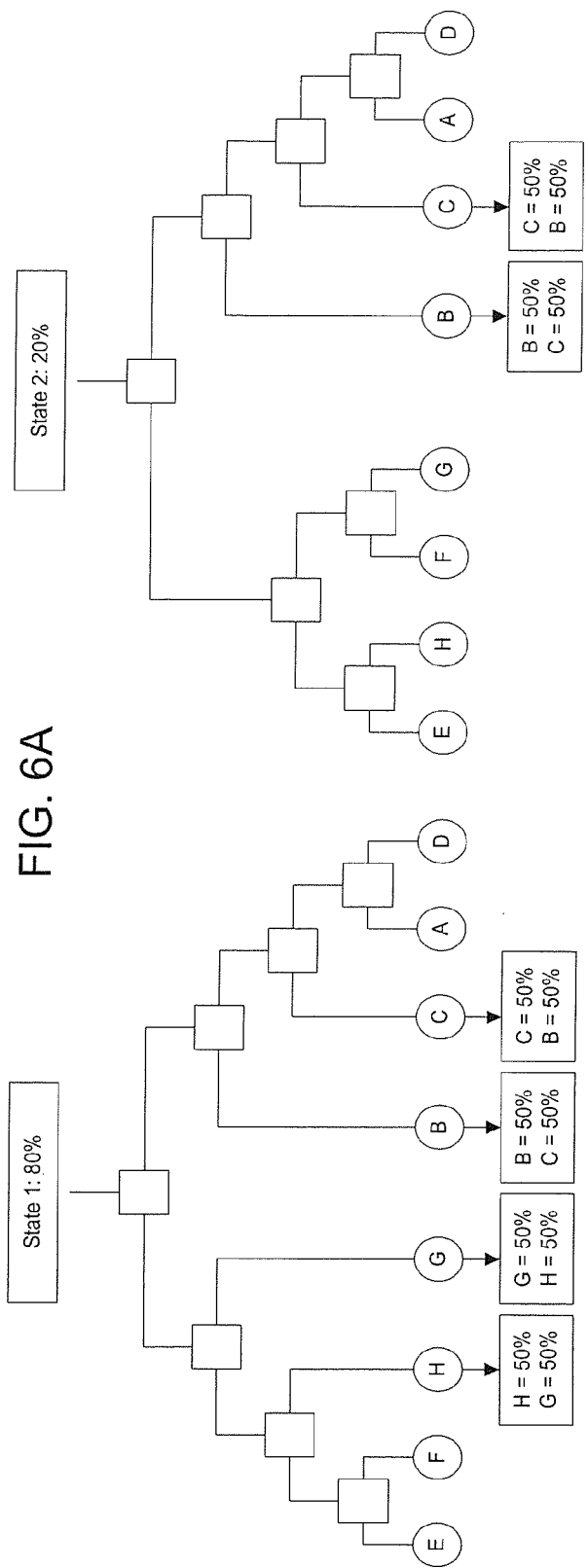
FIG. 6C
FIG. 6B

SYSTEM AND METHOD FOR MODELING AND ANALYZING DATA VIA HIERARCHICAL RANDOM GRAPHS

BACKGROUND

Networks or graphs are useful in describing and quantifying relationships between entities in a broad variety of complex systems, such as the world wide web, the Internet and social, biochemical and ecological systems. Studies suggest that networks often exhibit hierarchical organization, where vertices divide into groups that further subdivide into groups of groups, and so on. In many cases, these groups are found to correspond to known functional units, such as ecological niches in food webs, modules in biochemical networks, or communities in social networks. Network analysis has hence been widely and successfully used in areas such as intelligence data analysis, social network analysis, Internet data processing, authorship networks, bioinformatics and medical data processing, and many others.

A hierarchical random graph (HRG) is a useful tool for clustering nodes in network graphs according to their connectivity with one another. The basic HRG algorithm was developed by Aaron Clauset, and employs Markov Chain Monte Carlo (MCMC) simulation methods to compute a population of binary trees, called dendrograms. The general HRG concept is described in further detail in Clauset et al., "Structural Inference of Hierarchies in Networks," Airoldi, E. M. et al. (eds.), *IMCL* 2006 *Workshop, Lecture Notes in Computer Science* 4503; 1-13 (2007), and Clauset et al., "Hierarchical Structure and the Prediction of Missing Links in Networks," 453 *Nature* 98-101 (May 2008), the content of both of which are incorporated herein by reference.

In general terms, given a network graph G with n vertices, a dendrogram D is a binary tree with n leaves corresponding to the vertices of G, in which pairs of nodes are organized according to their connectivity in the network and closely emulate the structure of the original network. Each branch of the tree only has two children. The nodes of the network naturally cluster themselves in the tree by placing nodes that are very closely connected in the network close to one another in the dendrogram. That is, such nodes share a very low-level common branch. Nodes that are less connected, however, share a higher-level branch. Nodes that are very far apart are connected at the highest level of the dendrogram. A hierarchical random graph is a combination of a dendrogram along with its probabilities.

FIGS. 1A-1B are respectively a schematic diagram of a network graph and a schematic diagram of a corresponding dendrogram generated via the traditional HRG algorithm. Initially, nothing is known about the network except for the connectivity of the nodes. This is analogous to the network graph of FIG. 1A without any shading. At this initial stage, the network is disorganized and difficult to interpret. After processing the network into a dendrogram, the connectivity of the nodes becomes much clearer. It is possible to see the relationships between nodes based on the height of their common branch. For example, the dendrogram contains a group of three nodes 120. The two nodes to the right are connected at the lowest level, while the one node to the left is connected at the next level. These nodes are relatively far from another group of nodes 121 at the far right of the dendrogram; their common branch is at the top 122, indicating that they are not strongly related in the network.

After the dendrogram is generated, one can color code or shade the nodes in the network graph based on their closeness. The shading in FIG. 1A is the result of the clustering by the dendrogram. Thus, computing a dendrogram allows an individual to easily see the relationships in the network data, which might not be apparent from simple inspection of the network graph.

One drawback of the traditional HRG framework is that it is only applicable to simple networks in which the links between nodes exhibit an all or nothing behavior. That is, in the traditional HRG algorithm, either two nodes in the network are connected fully, or they are not connected at all. This limits the utility of the HRG algorithm to an extremely small subset of network science problems, such as those in ecology. For problems that require the analysis of networks where nodes have different connection strengths, or those networks which connectivity changes over time (e.g., social networks, etc.), the application of traditional "all or nothing" HRG is insufficient.

There are plenty of networks where links between nodes must be expressed in terms of a weight, such as, for example, to express quantity of goods flowing through a supply chain network, frequency of communication in e-mail networks or cell phone networks, and many others. In addition, when dealing with dynamic networks in which the links between nodes change as a function of time and activity, one must be able to express the strength of the connections between nodes as a continuous variable.

There are two possible ways to apply the traditional HRG algorithm to networks in which the connections have variable strengths, such as the weighted and dynamic networks. The simplest method is to consider all nonzero weights as generic connections. The actual weights of these connections must be handled internally by the algorithm, but do not affect the calculation of dendrograms during the MCMC process. The problem with this method is that it does not differentiate between very strong and very weak connections. That is, a connection with strength 0.99 would exhibit the same connectivity as a connection with strength of 0.01, which would eliminate the ability for connections to compete against one another in the dendrogram population.

An alternative approach to thresholding the connections at zero is to have a variable threshold in which all connections with a weight greater than this threshold are considered connected, while those whose connection strengths fall below this threshold are considered disconnected. While this is an improvement from the threshold-at-zero approach, this is still insufficient.

Another drawback of the original HRG framework is that it exclusively concerns networks having only one kind of relational attribute between network nodes. There are, however, many circumstances where multiple kinds of attributes between nodes are present. For example, the relation between two people in a social network may be revealed by both physical meetings and electronic communications (phone calls, emails, etc.). The original HRG framework can deal with such networks by 'flattening' the multiple attributes into a single quantity. One example of such flattening is to simply compute an average of multiple attributes, to come up with a single number (a weight). However, much information is lost by flattening the attributes into a single weight.

Accordingly, what is desired is a system and method for clustering nodes in network graphs that takes into account the strength of the connection between two nodes, as well as multiple attributes that may be present between the nodes. Such a system and method may be desirable to model and analyze multi-modal, relational, and spatial-temporal, and multi-layered data to discover mixed communities from multi-layered relationships within the dataset.

SUMMARY OF THE INVENTION

According to one embodiment, the present invention is directed to a data processing apparatus and a computer implemented method for modeling and analyzing relational data represented in a network that includes a plurality of nodes and a plurality of connections between the nodes. The data processing apparatus includes a processor and a memory or any other non-transitory computer readable medium. The memory stores program instructions that are executed by the processor for causing the modeling and analysis of the relational data.

According to one embodiment of the invention, the method for modeling and analyzing relational data includes assigning at least one weight to a connection between two nodes in the network. A set of possible dendrograms is then generated for the network, and a likelihood of each dendrogram in the set is determined. The determination of the likelihood is based on at least the one weight of the connection. One of the dendrograms from the set is selected as an optimal dendrogram based on the determined likelihood. The selected dendrogram is then output via an output device.

According to one embodiment of the invention, the weight is reflective of a strength of the connection between the two nodes in the network.

According to one embodiment of the invention, the connection is associated with an attribute, and the weight is a measure of the attribute.

According to one embodiment of the invention, the connection is associated with a plurality of attributes. A weight is assigned to each one of the plurality of attributes. The determination of the likelihood of each dendrogram in the set is based on the weight of each one of the plurality of attributes.

According to one embodiment of the invention, the attribute is a dynamic attribute configured to change over time. The weight may then be a function of time.

According to one embodiment of the invention, a plurality of attributes and values for the attributes are extracted from a dataset, and a network is generated based on the plurality of attributes. The plurality of attributes are represented as a single connection between two nodes in the generated network. Each of the plurality of attributes are associated with a weight based on an extracted value. The likelihood of each dendrogram in the set is then based on the weight of each one of the plurality of attributes.

According to one embodiment of the invention, a missing or noisy attribute is identified in the single connection between the two nodes. The detection may also be that a connection is missing between particular two nodes in the generated network, or that the connection between particular two nodes in the generated network is a noisy connection.

According to one embodiment of the invention, the selected dendrogram provides a hierarchical community structure denoting connectivity in the generated network.

A person of skill of art should recognize that embodiments of the present invention allow for modeling and analyzing of relational data. More specifically, the claimed system and method allows for the generating of hierarchical clusters of the data and prediction of missing links or identification of any possible false-positive (noisy) links within the relational dataset. Applications of the embodiments of the present invention include, for example, analyzing product data (e.g. warranty data processing) or customer relations data (e.g. monitoring opinions).

These and other features, aspects and advantages of the present invention will be more fully understood when considered with respect to the following detailed description, appended claims, and accompanying drawings. Of course, the actual scope of the invention is defined by the appended claims.

BRIEF DESCRIPTION OF THE DRAWINGS

FIG. 6A-6C is a schematic diagram of a "control" network graph and optimal dendrograms in equilibrium for the network according to one embodiment of the invention;

DETAILED DESCRIPTION

Figures 1A, 1B:
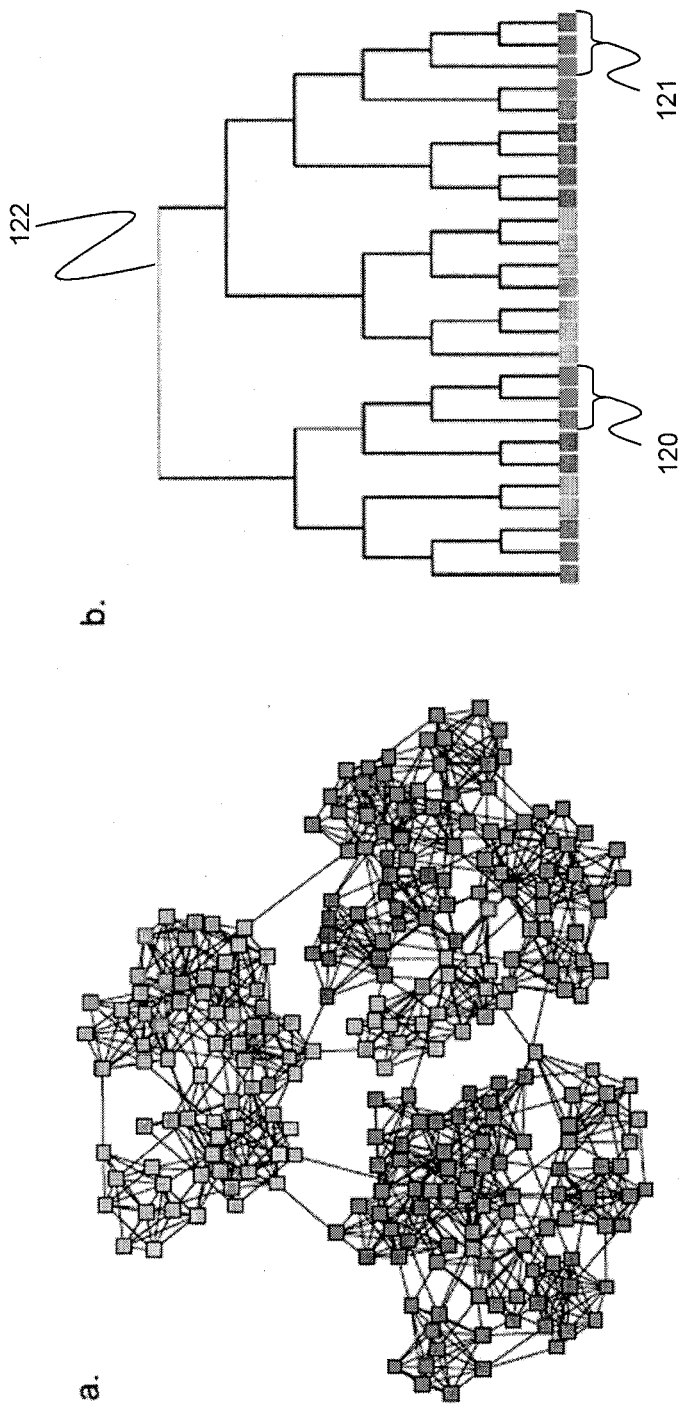
FIGS. 1A-1B are respectively a schematic diagram of a network graph and a schematic diagram of a corresponding dendrogram generated via a traditional HRG algorithm.

An embodiment of the present invention is directed to a system and method for data mining via hierarchical random graphs. For example, the hierarchical random graphs allow for clustering and analyzing of unorganized, sometimes disparate, network data. Embodiments of the present invention allow the analysis of different types of connectivity between nodes in such an organized network that cannot or should not be characterized as all or none, but rather, characterized with a degree of connectivity. When such analysis is extended to a multi-layered network that models entity relations between multiple network layers, a hierarchical community structure with mixed membership can be recovered which would not be recovered by separate analysis of single-layered networks.

The structure is recovered in the sense that it existed in the real-world environment, and that structure is now discovered by analyzing the data.

An embodiment of the present invention extends the algorithm employed by the traditional hierarchical random graph (HRG) paradigm to provide an enhanced HRG that accommodates networks with weighted links between the nodes of the network (also referred to as the weighted HRG or wHRG). This permits the HRG algorithm to be applied to an entirely new class of networks and problems. Such applications include, but are not limited to, networks which nodes have degrees of connectivity (such as social networks, where some people communicate more with some people than others), and dynamic networks, whose links change as a function of time.

According to one embodiment of the invention, the weights are associated with a single type of relational attribute between the network of nodes. According to another embodiment of the invention, the enhanced HRG framework takes into account multiple relational attributes between the network of nodes. The multiple attributes are realized in the form of a vectorized link weight, where each component of the vector represents one attribute. The enhanced HRG framework according to this latter embodiment, which is also referred to as the vectorized HRG or vHRG, takes into account the multiple relational attributes and extracts clusters of network nodes so that the multiple relations may be reflected at different levels of the cluster hierarchy, taking advantage of the major benefit of the original HRG.

According to one embodiment of the invention, the vectorized HRG is used for discovering a hierarchical community structure with mixed membership from a spatial-temporal data stream of human activities, such as, for example, communication and meeting events. A hierarchical community is a community composed by a hierarchy of smaller communities. For example, a company may have several business units, each of which may have several departments, each of which may have several groups, and each of which may have several members. A member may have the characteristic of mixed membership, i.e., a member can belong to more than one hierarchical community; for example, in matrix organization, a member could be in one department and at the same time belong to a workforce team which is orthogonal to the fixed hierarchy of organization.

Figure 2:
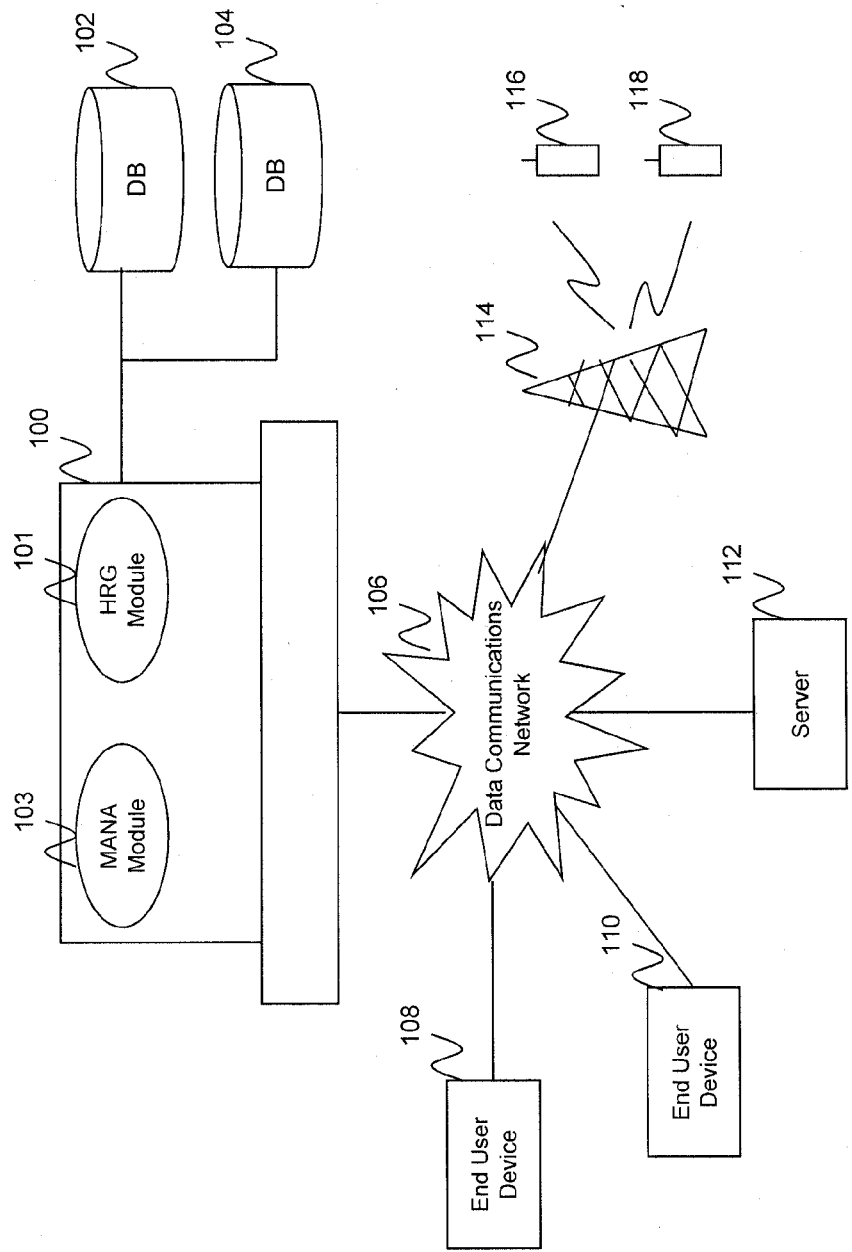
FIG. 2 is a schematic block diagram of a system for modeling and analyzing relational data represented in a network according to one embodiment of the invention.

FIG. 2 is a schematic block diagram of a system for modeling and analyzing relational data represented in a network according to one embodiment of the invention. The system includes a data processing apparatus 100 coupled to one or more end user devices 108, 110, servers 112, cellular networks 114, and/or other types of networks and devices, over a data communications network 106.

The end user devices 108, 110 may be terminal devices, personal computers, workstations, clients, mini-computers, mainframe computers, laptop computers, a network of individual computers, mobile computers, palm-top computers, hand-held computers, set top boxes for a television, other types of web enabled televisions, interactive kiosks, personal digital assistants, interactive or web enabled wireless communications devices, mobile web browsers, or a combination thereof. According to one embodiment, without implying a limitation, each of the end user devices 108, 110, 116, 118 include a microprocessor, memory, and input and output units.

The servers 112 may be one or more application servers, media servers, email servers, web servers, FTP servers, proxy servers, and the like. One or more of the end user devices 108, 110, 116, 118 may be used to access the servers 112. Each of the servers are also configured with one or more microprocessors, memory, and input and output units.

The data communications network 106 may be network or combination of networks spanning any geographical area, such as a local area network, wide area network, regional network, national network, and/or global network. The Internet is an example of a current global computer network. In addition, the communication network may be a hardwire network, wireless network, or a combination of hardwire and wireless networks.

According to one embodiment, the end user devices 108, 110 and/or handheld devices 116, 118 (for example and without implying a limitation, cellular phones, Personal Digital Assistants (PDA), e-readers, ipods, ipads etc.) may be used to communicate with different people by exchanging emails, text messages, phone calls, and/or scheduling meetings. Users may also communicate by accessing different types of social networks such as, for example, Facebook or LinkedIn. Such communication may be facilitated by the server 112, cellular network 114, or the like. Data exchanged in the communication may be monitored and stored by the server 112 and/or cellular network 114.

The data processing apparatus 100 may gather usage and communications data from the servers 112, cellular networks 114, and the like. Such data may be stored in one or more databases 102, 104. Other types of spatial-temporal data of human activities may also be monitored directly or indirectly by the data processing apparatus, and stored in the databases 102, 104.

According to one embodiment of the invention, the data processing apparatus 100 includes one or more microprocessors, memory, and input and output devices. The one or more input devices may include, for example, a keyboard, mouse, touch pad, joystick, electronic pen, and the like. The output devices may include, for example, a visual display screen and an audio output. The data processing apparatus also includes a local, global, or wide area interface link to receive and transmit data to and from the various devices with which it communicates.

According to one embodiment, the data processing apparatus 100 includes an HRG module 101 and a multi-layered adaptive network analytics (MANA) module 103. A person of skill in the art will recognize that the two modules may be combined into a single module or divided into other sub-modules. Each of the modules may be implemented via one or more ASICs, FPGAs, programmed microprocessors and/or the like, that are configured to perform the specified functions of HRG and MANA modules. For example, the microprocessors may be coupled to a memory storing computer instructions which, when executed by the microprocessor, allow the specified functions to occur.

According to one embodiment of the invention, the HRG module 101 includes computer program instructions for the HRG, wHRG, and vHRG algorithms. The MANA module 103 includes computer program instructions for identifying one or more attributes from a dataset and building a network based on the identified attributes. The MANA module 103 then invokes the HRG module 101 to build a hierarchy for the generated network. The network that is built by the MANA module 103 may be single-layered or multi-layered networks.

Hierarchical Random Graph for Networks with Weighted Edges

The traditional HRG algorithm involves the random generation of candidate dendrograms, and the evaluation of each of the generated dendrograms by computing its likelihood based on the structure of the network. From a randomly chosen initial dendrogram, the algorithm computes the likelihood of the dendrogram based on its structure and the connectivity between the sides of each binary split. Highly connected regions in the graph are more likely to be grouped together in the dendrogram, whereas barely connected regions are less likely to be located near one another in the dendrogram.

While the traditional HRG algorithm is adept at computing the most likely dendrogram for the network graph whose links follow an all or nothing binary classification, it cannot cope with more complicated networks which nodes exhibit various degrees of connectivity.

According to one embodiment of the invention, the weighted HRG algorithm accommodates networks with weighted links between nodes. In this regard, the algorithm performs a guided random search over the set of possible dendrograms for a given network that takes into account the weights of the connections, and converges to an optimal dendrogram for the network. The likelihood of the dendrogram is a measure of the goodness of fit between the network graph and the dendrogram structure, based on how well the connections in the network graph are represented in the dendrogram. While the likelihood can theoretically be equal to 1 (indicating a perfect match between the dendrogram and the network), the best/optimal dendrogram for a given network generally has a likelihood that is less than 1. This is because there is a great deal of compromise involved when computing a dendrogram. Since each branch can only accommodate two nodes at a time, it is likely that there are many equally-good dendrograms for a given network. For example, in FIG. 1B, if the three nodes 120 might be equally connected with one another in the network, but only two can be connected at the lowest level, the third must connect at the next level. Consequently, there may be many dendrograms with the same likelihood for the same network graph.

Figure 3:
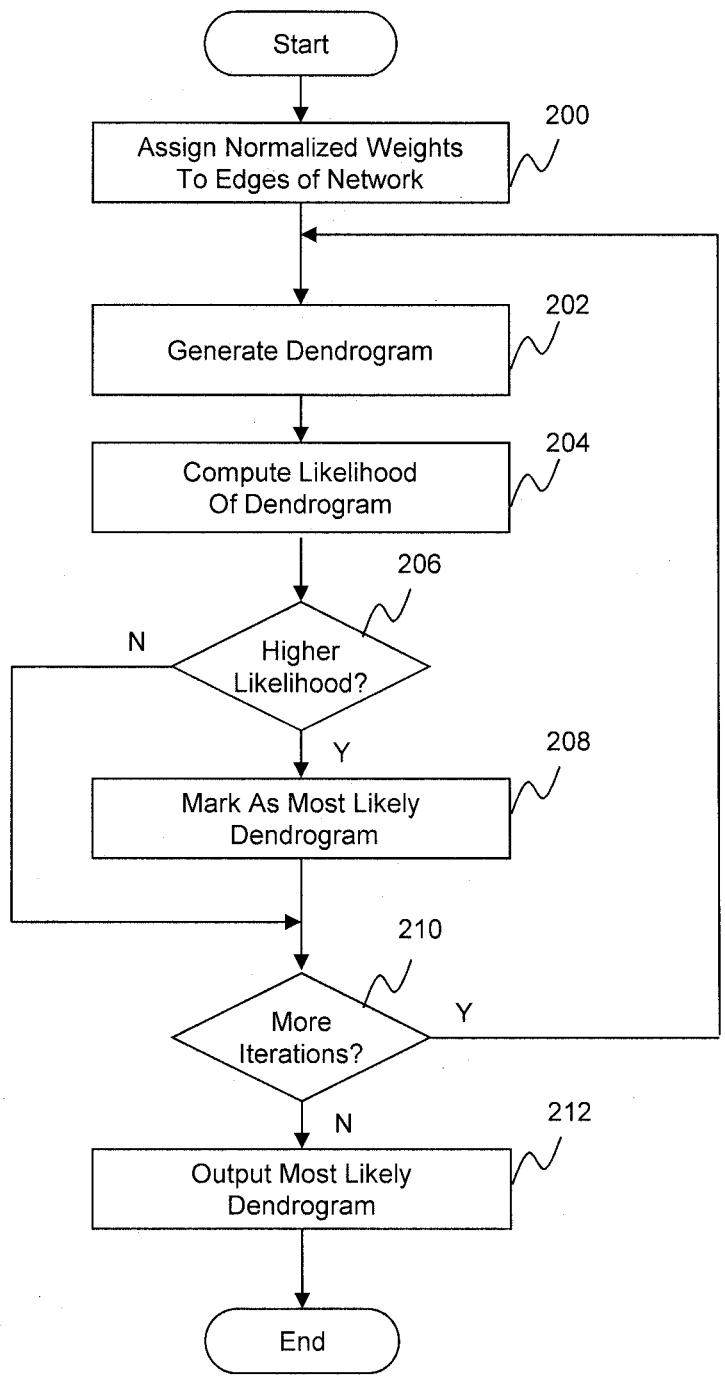
FIG. 3 is a process flow diagram of a weighted HRG algorithm implemented by an HRG module for clustering nodes in a network where links between the nodes are weighted, according to one embodiment of the invention.

FIG. 3 is a process flow diagram of a weighted HRG algorithm implemented by the HRG module 101 for clustering nodes in a network where the links between the nodes are weighted, according to one embodiment of the invention. The steps of the process may be executed in the indicated order or in any other order recognized by a person of skill in the art.

The process starts, and in step 200, the HRG module 101 assigns normalized weights to the edges (also referred to as links or connections) of the network. The weights may reflect a strength of a connection (or degree of connectivity) between two nodes of the network where the connection is associated with a particular attribute. Thus, the weight may be deemed to be a measure of the attribute. For example, the weight may reflect a frequency of communication between two people represented as the nodes of the network, a duration of the communication, a strength of their friendship, a frequency of personal meetings, and the like.

In assigning the weight, the HRG module 101 normalizes all connections in the network to a value within a predetermined interval. Since the likelihood model for HRG employs probability measures, the weights are expressed in such a way that preserves their compatibility with probabilistic modeling. Therefore, the weights of all connections between nodes are normalized to a range between, for example, zero and one. According to one embodiment, this is done by normalizing all network weights by the maximum value. As a result, the maximum value is normalized to the value of one, and all values below the maximum value are assigned a value less than one. If and when the connection weight between two nodes is equal to zero, as might be the case in a dynamic network, the connection is removed from the graph and ignored in subsequent steps in the algorithm. Of course, a person of skill in the art will understand that other normalization techniques conventional in the art are also possible.

In step 202 of FIG. 3, the HRG module 101 generates a random dendrogram configured to closely emulate the structure of the original network by running a Markov Chain Monte Carlo (MCMC) simulation method as described in the above-referred paper by Clauset et al. entitled "Structural Inference of Hierarchies in Networks." In generating every subsequent dendrogram after an initial dendrogram, the HRG module 101 invokes a random perturbation of a single split in the previous dendrogram. One of the split locations is randomly selected for the perturbation. Next, either the left or right subtree at this split is selected. The subtree is then subjected to either an "alpha" (swapping of branches) or "beta" (swapping of leaves) move at its top-level split, which is again randomly selected. Consequently, the new dendrogram represents a slight but palpable variation on the previous dendrogram, and facilitates an organized random walk through the dendrogram space.

Figure 4:
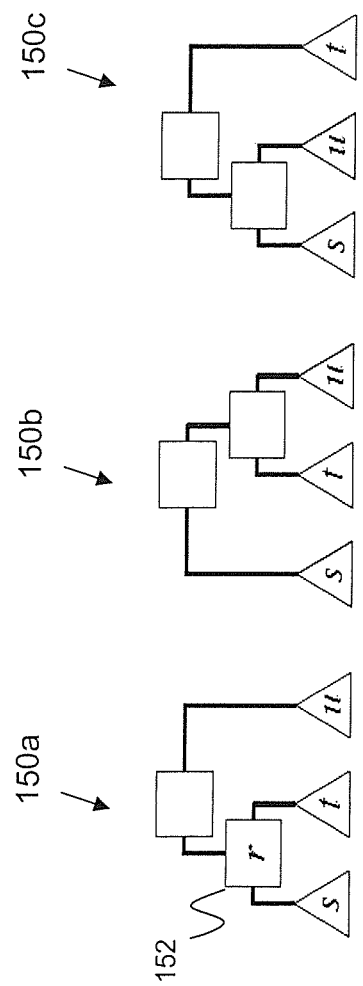
FIG. 4 is a schematic diagram of three dendrograms depicting how subtrees are defined in a network graph according to a split/branch in the dendrogram.

FIG. 4 is a schematic diagram of three dendrograms 150a, 150b, 150c depicting how subtrees are defined in the network graph according to the split/branch in the dendrogram. Dendrogram 150a is an initial representation of the network, and dendrogram 150b is a result of an alpha move of dendrogram 150a at a randomly selected split 152, while dendrogram 150c is a result of a beta move of dendrogram 150a at the same split.

In searching for the optimal dendrogram, the HRG module 101 computes, in step 204, the likelihood of the current dendrogram. Since the number of branches in the dendrogram is fixed as a function of the number of nodes in the network, only the positions of the nodes at each branch must be optimized. In this regard, unlike the traditional mechanism for optimization, the weighted HRG algorithm takes into account the weights of the edges in computing the likelihood of each dendrogram. Specifically, unlike the traditional mechanism that expresses a given probability p of a branch in the dendrogram as the fraction of edges that exist between two subtrees with respect to the number of possible edges between those subtrees, the weighted HRG algorithm instead uses a weighted sum of the edges between the subtrees relative to the maximal number of connections. Thus, the probability $p_i$ of a split i in a current dendrogram may be expressed as:

$$p_i = \frac{\sum_{j=1}^{E_i} w_j}{L_i R_i}, \quad (1)$$

where L and R are the number of nodes in the left and right subtrees produced by the split, respectively, and $E_i$ is a total number of edges that span the left and right subtrees. In this scenario, $w_j$ represents the weight associated with a given edge that spans the separation between subtrees. The numerator in the above expression is the sum of the weights that span the two subtrees created by the split. The denominator is the maximum number of connections of weight "1" that can span the subtrees. The number of connections from the nodes in the left subtree to the nodes in the right subtree is simply the product of $L_i$ and $R_i$. Therefore, the maximum value of $p_i$ is 1. This maintains consistency with the original algorithm, since the probability of at any dendrogram node within a network whose edge weights are all unity will be equal to the number of edges that span the left and right subtrees. In other words:

$$\sum_{j=1}^{E_i} w_j = E_i \quad (2)$$

when all $w_j$ are equal to one. The derivation of the likelihood, K, of dendrogram D is the same as in the original algorithm:

$$K = \prod_{i \in D} \{p_i^{p_i}(1-p_i)^{1-p_i}\}^{L_i R_i} \quad (3)$$

The likelihood of the dendrogram in light of the connections in the original network graph is computed for each random dendrogram.

Referring back to FIG. 3, in step 206, a determination is made as to whether the dendrogram has the highest likelihood so far based on the comparison of the currently computed K. If the answer is YES, the dendrogram is stored, logged, or tagged as the most likely dendrogram in 208 and the next iteration is applied to it. If the dendrogram has a lower likelihood, it is discarded and next iteration is applied to the previous dendrogram. If the dendrogram has the same likelihood, it may be discarded or used in the next iteration.

According to one embodiment of the invention, the HRG module 101 stops the search after the algorithm has processed a given number of iterations without finding a better dendrogram. According to another embodiment, the HRG module 101 stops the search after a certain number of iterations 210. In this regard, in step 210, a determination is made as to whether there are more iterations of the MCMC to be performed. The number of iterations to be performed may, for example, be arbitrarily selected by the HRG module 101. If there are more iterations to perform, the process returns to step 202 to generate another dendrogram based on a next iteration of the MCMC approach.

After all iterations have been performed, the HRG module 101 outputs 212 one or more dendrograms with the highest likelihood as the best representation of the network for that particular time. At this point, the MCMC has reached an equilibrium and the output dendrogram(s) is deemed to be the optimal dendrogram for the network. The output dendrogram may be displayed on the display screen, saved in a secondary memory, or further used by the HRG module 101 to cluster the nodes in the network for further analysis of the network data. The display or clustering of the nodes may be done in response to a user input via the input device.

One of the benefits to the weighted HRG approach is the ability to support dynamic networks which connections change as a function of time. This may be important when applying the weighted HRG algorithm to social networks, whose connections are in a constant state of flux. In this case, the connection strength (weight) between nodes in a graph is expressed as a function of time. This may be accomplished, for example, by describing each connection between nodes a first-order differential equation:

$\dot{w}(t) = k\, w(t) + x(t)$, where k is a constant and w(t) represents the strength of the connection as a function of time, t. The variable x(t) indicates input to the system that reinforces the connection between two nodes in the graph.

The ability to use weighted values to describe the connections between nodes can be used to significantly improve the analysis of a dynamic network. Variations in connection strength are helpful to such an analysis, since cursory or incidental connections between nodes in the network can eventually be allowed to fade into the background, while habitual or intense connections strengthen under this paradigm. This idea contrasts with other common methods of dynamic network analysis, in which links of unity weight are added and removed between nodes without any specific notion of connection strength.

A person of skill in the art would recognize that the present invention is not limited to the use of a first-order differential equation model in order to take into account dynamic networks where connections change as a function of time. The first-order differential model could be replaced by a more complicated differential or difference equations, or a completely different family of mathematical descriptions to clarify the relationship between the connection strength, additional connections from other nodes, and time, as will be apparent to a person of skill in the art.

Figure 5:
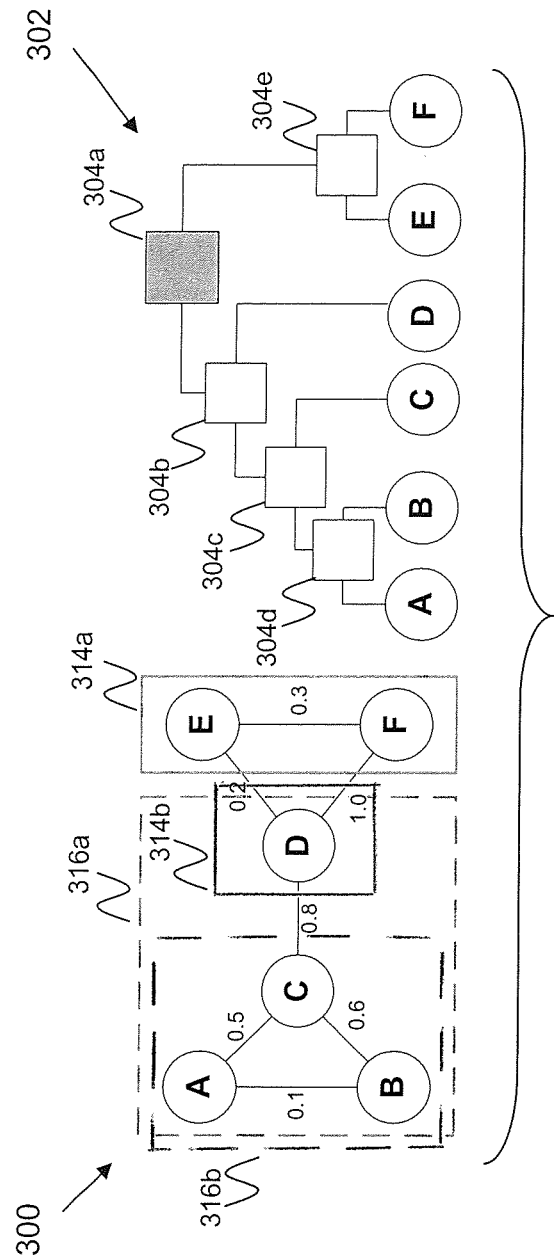
FIG. 5 is a schematic diagram of an exemplary network graph with weighted connections between nodes, and a dendrogram generated for the network graph, according to one embodiment of the invention.

FIG. 5 is an exemplary network graph 300 with weighted connections between nodes, and a dendrogram 302 generated for the network graph, according to one embodiment of the invention. Each split 304a-e in the dendrogram 302 has a corresponding probability $p_i$, which allows the computing of the likelihood of the dendrogram. In the illustrated example, a solid line is drawn to identify the right subtrees 314a, 314b, and a dashed line is drawn to identify the left subtrees. The probability associated with split 304a associated with right subtree 314a and left subtree 316a is (1.0+0.2)/(4*2)=0.15 based upon formula (1). The probability associated with split 304b associated with right subtree 314b and left subtree 316b is 0.8/3*1=0.27. The likelihood of the dendrogram 302 itself may then be computed according to after the probability of the remaining splits 304c-304e is computed based upon formula (3).

To illustrate the added utility that a weighted HRG algorithm brings to the field of network science, a number of network graphs were analyzed using various weights between network nodes. Two examples illustrate how the addition of weights to the HRG algorithm dramatically improves its utility in practical network analysis problems.

The first example illustrated in FIG. 6A is a "control" network graph, whose weights have been set to unity. This network was processed by the weighted HRG algorithm for multiple trials; this was done in order to determine the nature of any equivalent dendrogram structures with equally-optimal likelihood values. For simplicity, a relatively simple network was chosen consisting of a pair of squares connected along their perimeter and once across the diagonal, with a final connection between the squares.

This first experiment was performed using both the regular HRG algorithm (no weights) and the proposed wHRG algorithm with all weights set to one. One would expect that these algorithms yield the same result, which they do. This particular network yields two optimal dendrograms in equilibrium. The first state illustrated in FIG. 6B occurs with frequency of about 80%, while a second state illustrated in FIG. 6C occurs with frequency of 20%; both states have identical likelihood. Within each state, there is a degree of interchangeability between the leaves in the dendrogram. This indicates the "equivalence" of the leaves in the hierarchy. For example, in the second state, the B and C leaves are equally interchangeable, even though they are at different levels of hierarchy in the dendrogram. This indicates that they are implicitly connected and clustered above the A/D pairing.

The high level of equivalence among dendrograms of equal likelihood is typically the result of competition between connections in the graph and the need to make decisions during the splitting process between different possible clustering patterns. As in chemistry where atoms of equal charge can attract electrons away from each other in a constant tug-of-war, producing "resonance structures", the dendrograms produced by a graph with many strong connections may yield many equivalent dendrograms of equal likelihood. In the illustrated example, the "resonance structures" are indicated by the boxes with arrows. These resonance structures are a result of competition between the edges in the graph. Because all the edges have the same weight in the graph, there arise a number of different dendrogram structure that can all yield the same likelihood.

FIGS. 7A-7B, 8A-8B, and 9A-9B display the results of running the wHRG algorithm on a set of weighted network graphs. In each of these cases, the same network graph structure and connections were used. However, the connection strengths between nodes was varied to show the effectiveness of wHRG and how taking the weights of the connections into account can have a dramatic effect on the dendrograms produced.

Figure 7A:
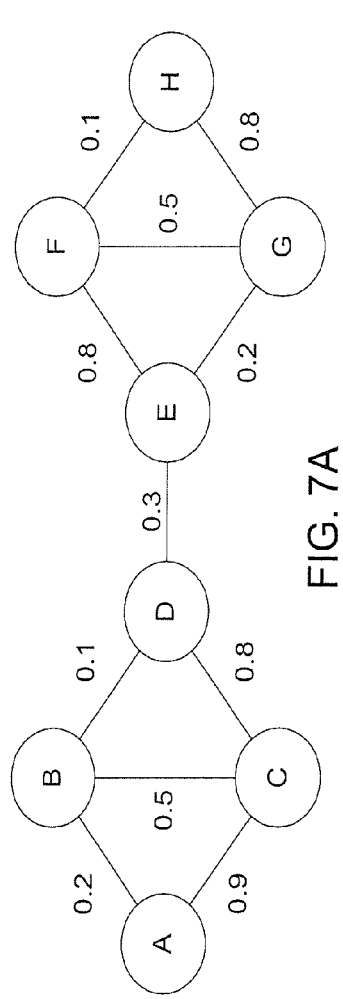
FIGS. 7A-7B, 8A-8B, and 9A-9B display results of running a wHRG algorithm on a set of weighted network graphs.
Figure 7B:
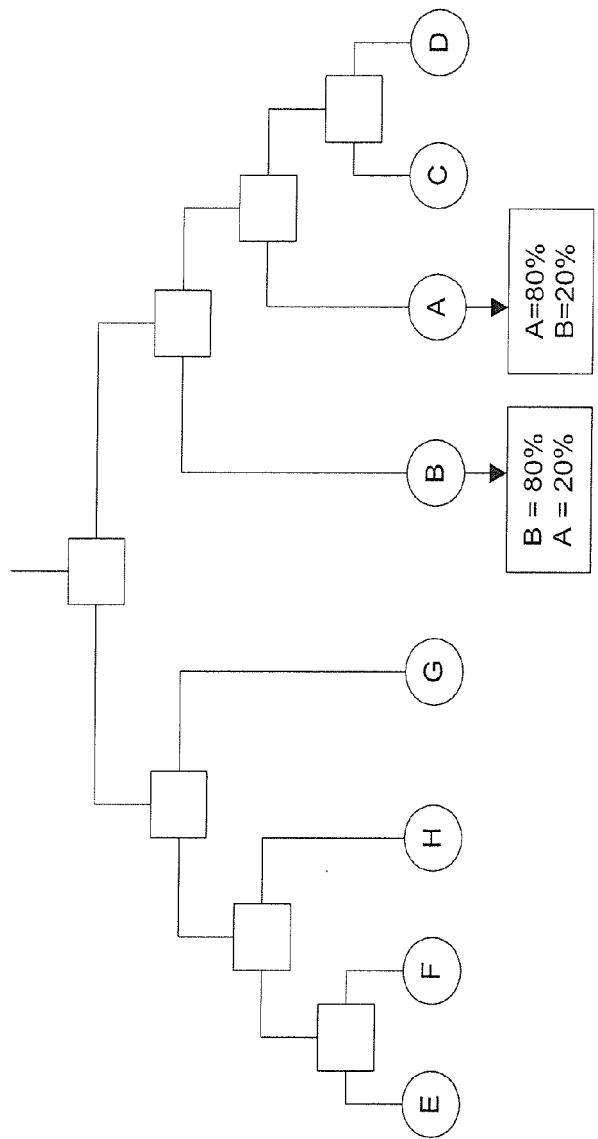

FIGS. 7A-7B illustrate an instance where the connection weights are altered in such a way that the wHRG algorithm produces a slightly different dendrogram pattern than that seen when the weights are all equally one. In this instance, there is only one optimal dendrogram structure, but there is still some resonance (alternate leaf positions) between A and B. This is a consequence of the weights in the network; instead of massive competition between a bunch of equal weights that can yield equivalent states, the gradation in the weights allows some dendrogram configurations to stand out while others fade into the background.

Figure 8A:
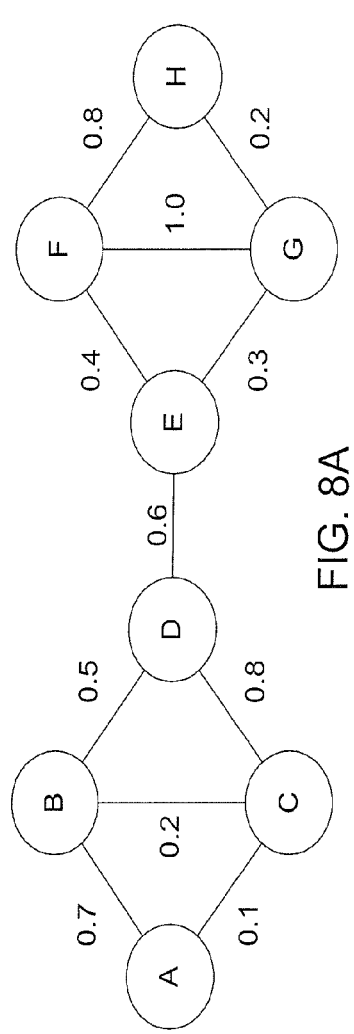
Figure 8B:
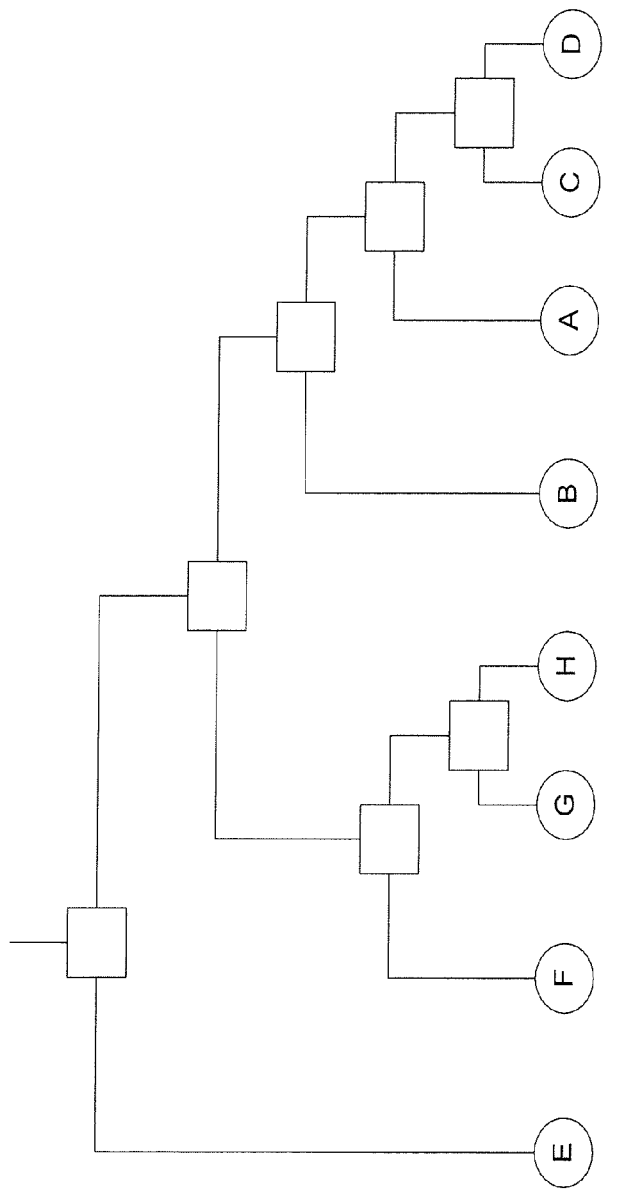

FIGS. 8A-8B illustrate this point. In this particular weighting configuration, there is only one optimal dendrogram. There are no alternate leaf positions in this case. Furthermore, the dendrogram structure yielded by this network is very different from the structure seen in FIGS. 6 and 7. This is likely due to the relatively strong connectivity between D and E with respect to the edges from E to F, and E to G. This results in the E leafs clustering far away from the rest of the dendrogram.

Figure 9A:
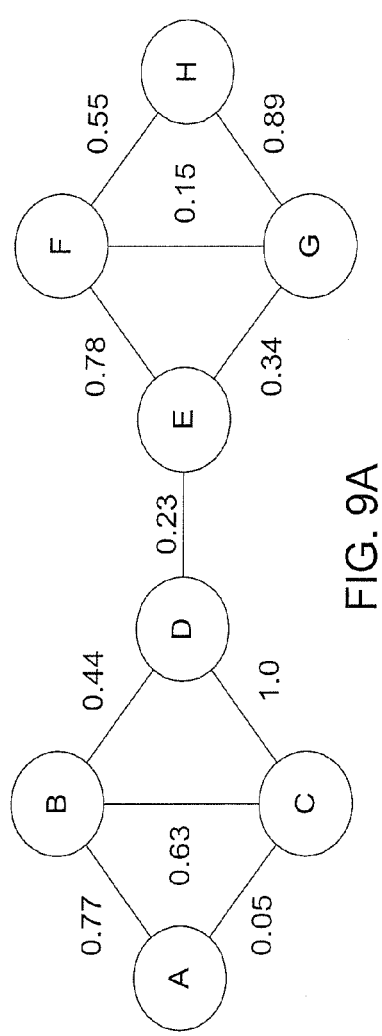
Figure 9B:
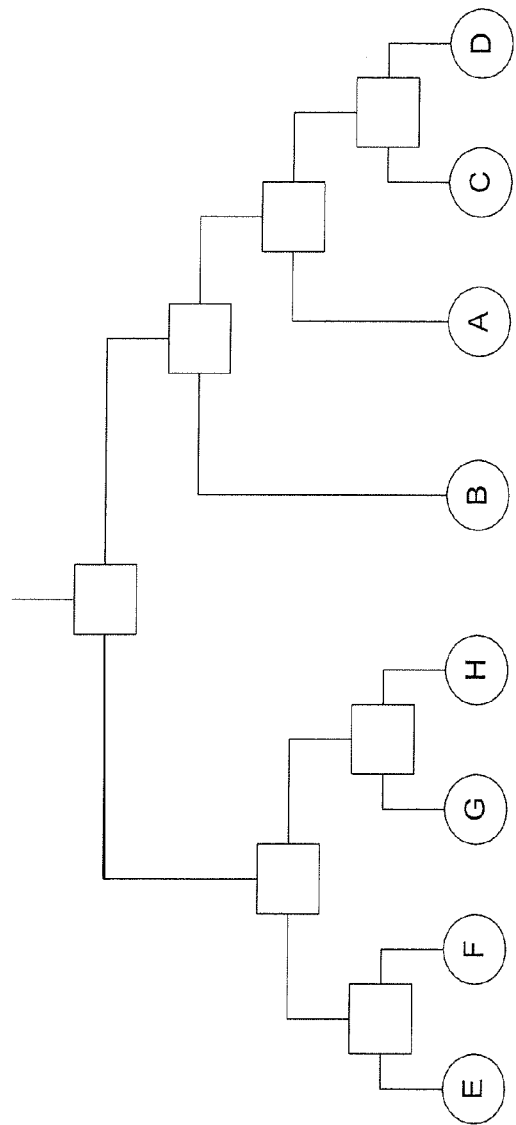

FIGS. 9A-9B provide yet another example of a weighted network whose optimal wHRG dendrogram differs from that provided by the traditional HRG algorithm. In this instance, the optimal dendrogram produced takes on a structure that is similar to the second resonance structure in the unity-weight example of FIG. 6. However, there is no equivalence between the leaves. Also, it is interesting to note that while the two sides of the graph are structurally similar, the difference in weights yields different hierarchies between the two sides.

In short, these examples show how critical the ability to handle weighted connections can dramatically change and improve the utility of hierarchical random graph methods.

Hierarchical Random Graph for Networks with Multiple Edge Attributes

Both the traditional HRG algorithm and the wHRG algorithm can only analyze networks having a single attribute. For example, assume that data on both physical meeting events and electronic communication events are identified and recorded between two people in a social network, possibly from mobile communication data. For the original HRG or the wHRG algorithm to analyze such data simultaneously and identify clusters, both attributes, that is, the relative frequency of physical meetings and the relative frequency of communications, are combined into a single weight reflecting a measure of the frequency of interaction between the two people. Such 'flattening' will form a single network structure and inevitably lose information, potentially causing some meaningful grouping of nodes to be lost.

Another approach would be to apply the HRG algorithm multiple times to the network, with considering only one kind of attribute at a time. Separate application of the HRG in this manner will generate multiple set of clusters independently, and the clusters can be analyzed together. However, the procedure simply ignores possible correlations among multiple cluster structures. For example, given a meaningful network component, each of different kinds of measured attributes may only reveal a too weak structure—though consistent over multiple attribute—to be extracted independently as a viable component. Both of the aforementioned approaches are not capable of systematically dealing with multiple network attributes and identifying clusters from those attributes in a synergistic manner.

According to one embodiment of the invention, a vectorized HRG (vHRG) algorithm analyzes multi-attribute network data and extracts hierarchical clusters that preserve those attributes. In this regard, multiple attributes between nodes are realized in the form of a vectorized link weight, where each component of the vector represents one attribute. The vHRG framework takes into account the multiple relational attributes and extracts clusters of network nodes so that the multiple relations may be reflected at different levels of the cluster hierarchy. The vHRG algorithm thus allows for hierarchical clustering of data with multiple weighted relations that does not require relations to be flattened or combined prior to clustering. That is, the algorithm analyzes all the attributes simultaneously, hence, is able to handle the correlations, whereas if it were to do it separately, it would not.

The vHRG algorithm is similar to the wHRG algorithm implemented via the process discussed with respect to FIG. 3, except for certain differences discussed below. Specifically, the weights are normalized as in the wHRG algorithm, except that there will be N such set of weights for N relational attributes. Random dendrograms are then generated through the MCMC approach as in the wHRG algorithm.

The vHRG approach computes the likelihood of the dendrogram for each link attribute. That is, the wHRG algorithm computes the likelihood score of each of the generated dendrograms; it computes the weighted sum of the edges between the subtrees relative to the maximal number of connections. The vHRG algorithm computes the likelihood of the given n-th attribute, in the same manner. When there are N attributes with weights $W_n\{w_{nj}|j=1, \ldots, K_n\}$, the computation of the likelihood to the n-th attribute starts with $$p_{ni} = \frac{\sum_{j=1}^{E_{ni}} w_{nj}}{L_{ni} R_{ni}} \qquad (4)$$

where L and R are the number of nodes in the left and right subtrees produced by the split, respectively. In this scenario, $w_{nj}$ represents the weight associated with a given n-th edge attribute that spans the separation between subtrees. Here, the probability that any dendrogram node within a network whose edge weights are all unity will be equal to the number of edges that span the left and right subtrees. In other words, $$\sum_{j=1}^{E_{ni}} w_{nj} = E_{ni}$$

when all $w_j$ are equal to one. The likelihood, $L_n$, of dendrogram D to the n-th attribute is:

$$L_n \Pi_{i \in D} \{p_{ni}^{P_{ni}}((1-p_{ni})^{P_{ni}}\}^{L_{ni}R_{ni}}$$

Each likelihood score $L_n$ represents the probability that the dendrogram D correctly reflects the hierarchical structure of the network constrained by the n-th attribute:

$$=P(D|n\text{-}th \text{ attributes})=P(D|W_n)$$

The final likelihood of the dendrogram that takes into account all of the N attributes is the probability of the given dendrogram representing the hierarchical network structure mandated by all of the N attributes:

$$L = P(D | \text{All attributes}) = P(D | W_1, \ldots, W_n) = \prod_{n=1}^{N} P(D | W_n) = \prod_{n=1}^{N} L_n$$

At the end of each iteration of the random walk, the likelihood of the dendrogram is compared to the likelihoods of all other dendrograms encountered up to that point. The random search is terminated after an arbitrary number of iterations, and the dendrogram(s) with the collection of dendrograms having likelihood above certain threshold are selected as the best representation of the network for that particular time step.

According to one embodiment of the invention, the HRG module 101 constructs and displays a consensus tree from the selected dendrograms. The algorithm for constructing the consensus tree is discussed in Bryant, "A Classification of Consensus Method for Phylogenetics," *DIMACS Series in Discrete Mathematics and Theoretical Computer Science* (2003), the content of which is incorporated herein by reference. The single consensus tree captures the estimated hierarchical structure of the network in a more concrete form. FIGS. 10B, 10C, 11 (ref 354) are examples of consensus trees.

According to one embodiment of the invention, the generated dendrograms may be analyzed for identifying missing or noisy attributes or links as is discussed in further detail below.

To illustrate the added utility that the current invention brings to the field of network science, a number of network graphs having various hierarchical structures due to multiple attributes were analyzed. Two examples illustrate how the disclosed features of the vHRG algorithm significantly enhance the hierarchical network analysis problem by uncovering previously hidden network structures.

Figure 10A:
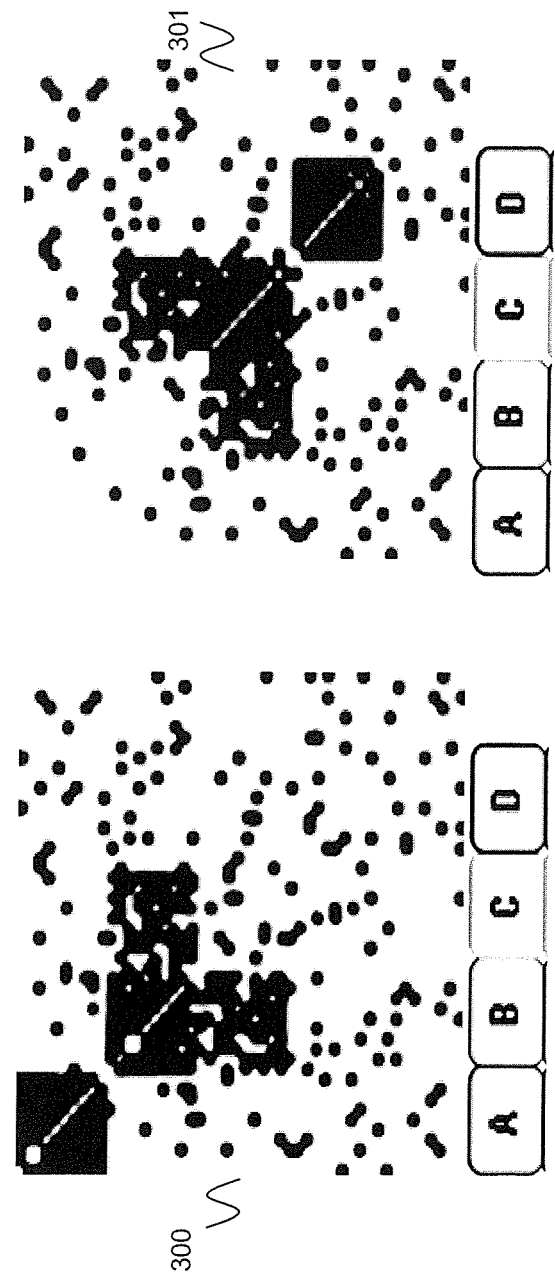
FIGS. 10A-10C are schematic diagrams that show how a vHRG algorithm enables extracting a hierarchical structure from a certain combination of multiple attributes, where a network component is constrained complementarily by two separate relational attributes.
Figure 10B:
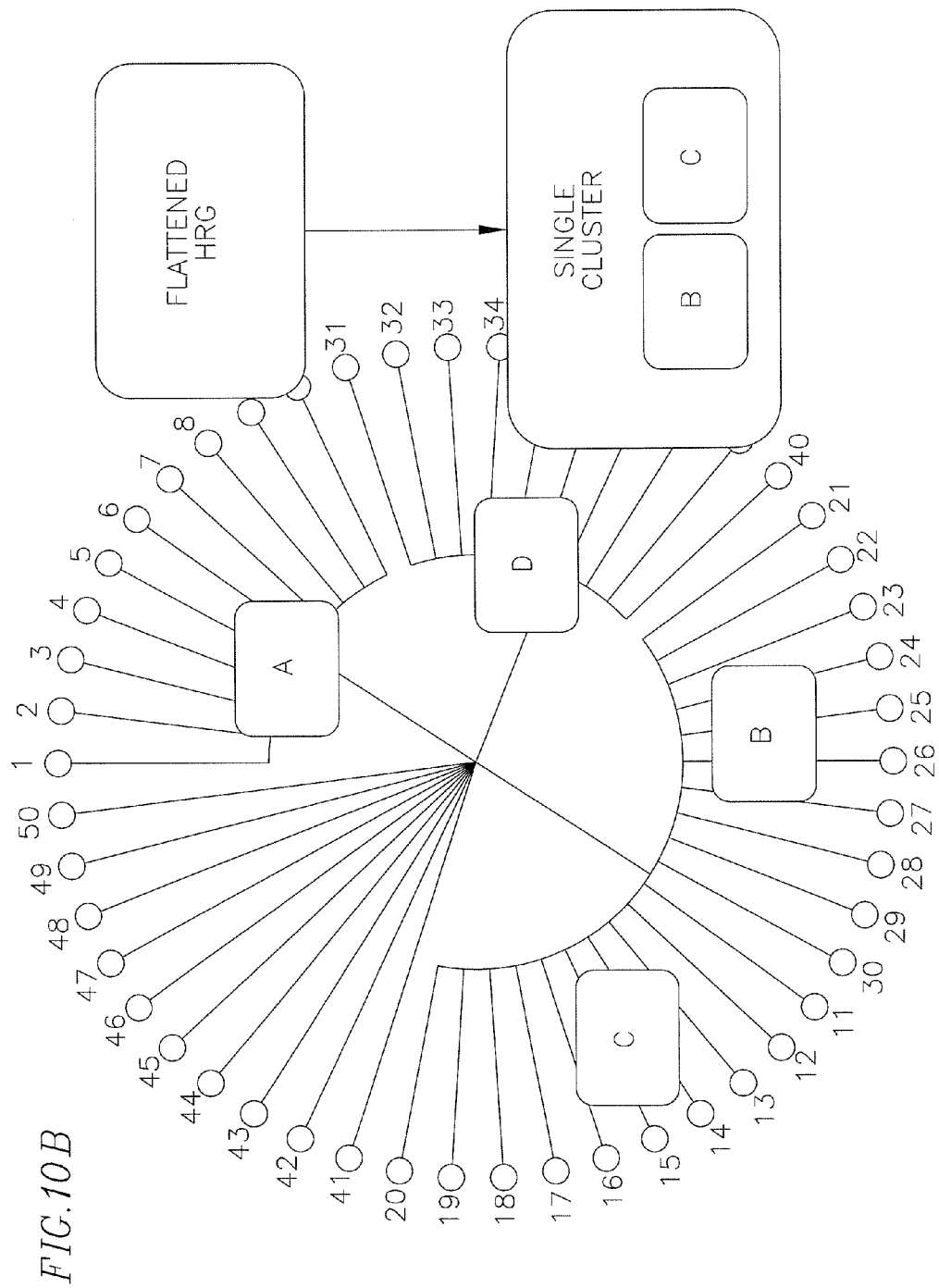
Figure 10C:
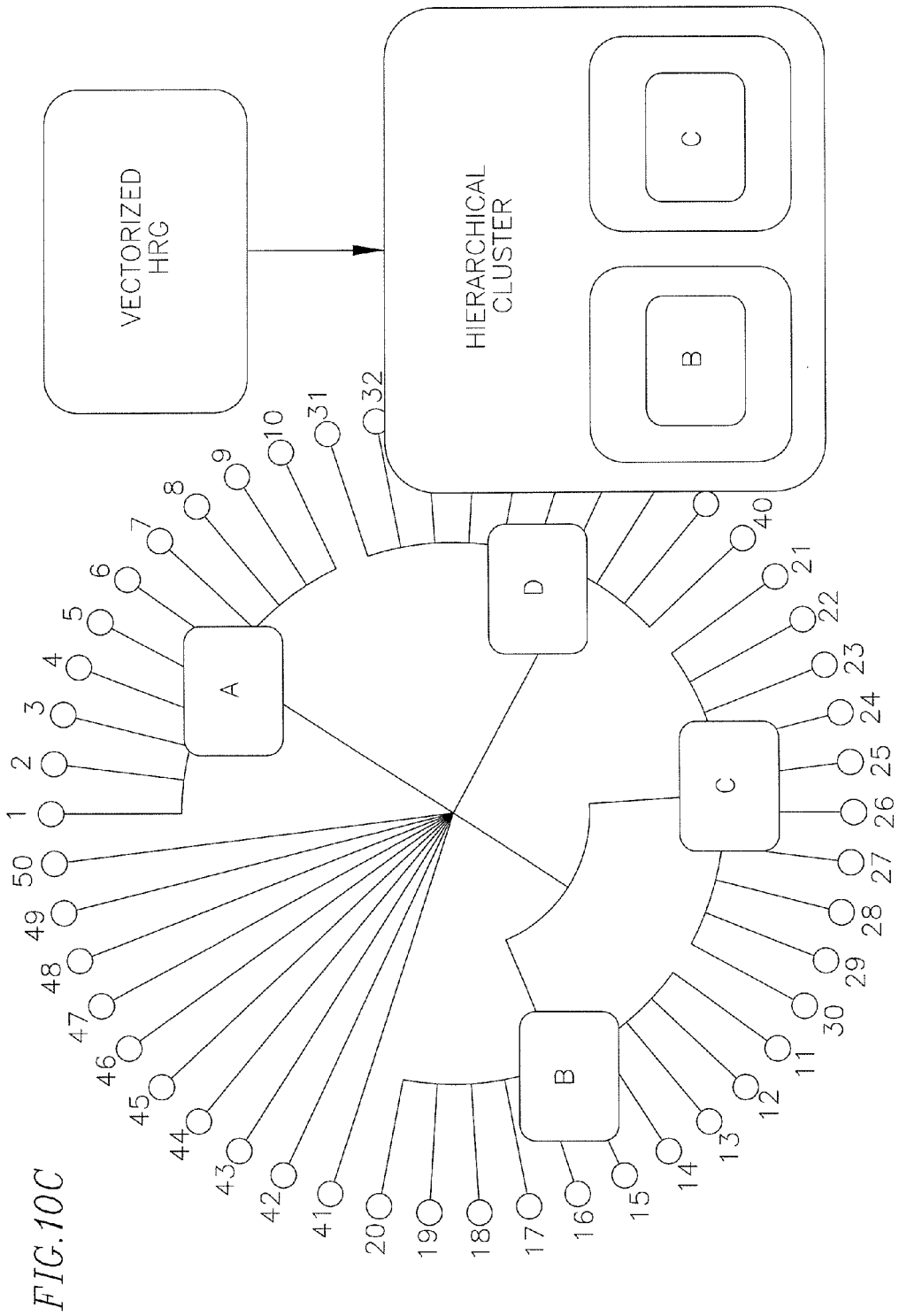

The first example illustrated in FIGS. 10A-10C are schematic diagrams that show how the vHRG algorithm enables extracting a hierarchical structure from a certain combination of multiple attributes, where a network component is constrained complementarily by two separate relational attributes. The exemplary network has fifty nodes along with two sets of weights, each corresponding to one of the two link attributes. Plots 300, 301 in FIG. 10A shows the two link attributes constraining clusters A, B, C, and D. More specifically, the dark pixels represent the existence of links between nodes, where the x-coordinate and the y-coordinate of a pixel are the node identities. The first attribute distinctly defines both the clusters A and B, but not the clusters C or D. The second attribute distinctly defines both the clusters C and D, but not the clusters A or B. Both the first and the second attributes constrain the relation between the cluster B and the cluster C in a complementary manner.

Both the regular HRG algorithm and the proposed vHRG algorithm were applied to the network. As previously stated, neither the original HRG nor wHRG algorithm can handle multiple link attributes. The two link attributes are simply averaged and merged to 'flattened' network links. The consensus tree generated from the wHRG algorithm is shown in FIG. 10B. The clusters B and C have been merged into a single cluster. On the other hand, the vHRG algorithm generated the consensus tree shown in FIG. 10C, where the clusters B and C are individually identified as well as the merged cluster {B, C} at the higher level.

Figure 11A:
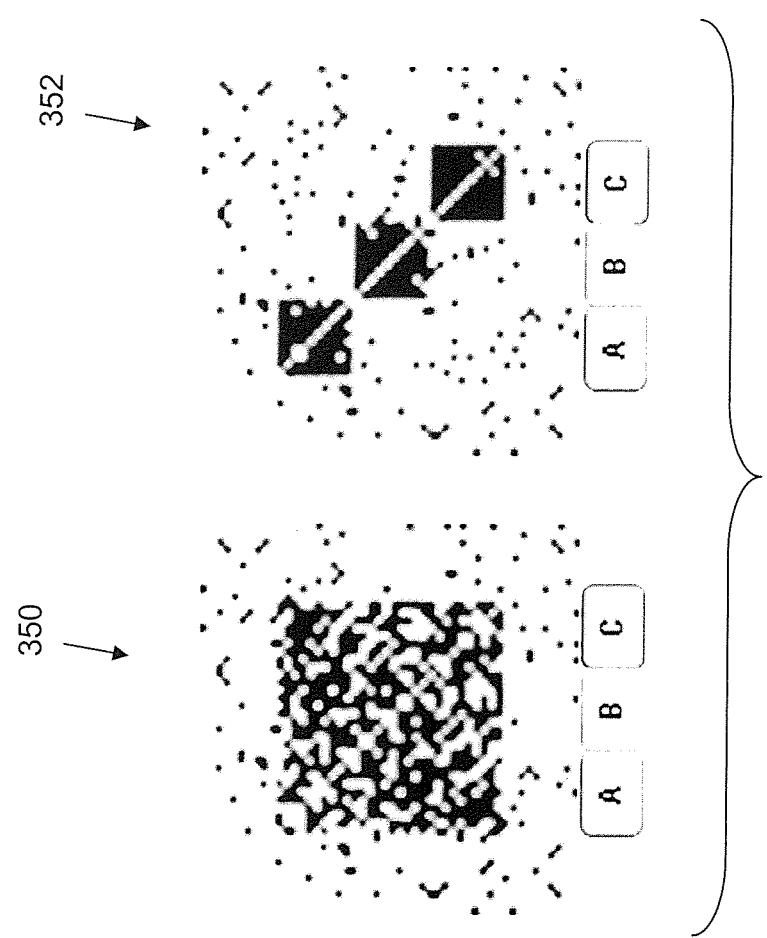
FIGS. 11A-11B are schematic diagrams that show how a vHRG enables extracting a hierarchical structure from a combination of network attributes, where a network component is constrained synergistically by two separate attributes.
Figure 11B:
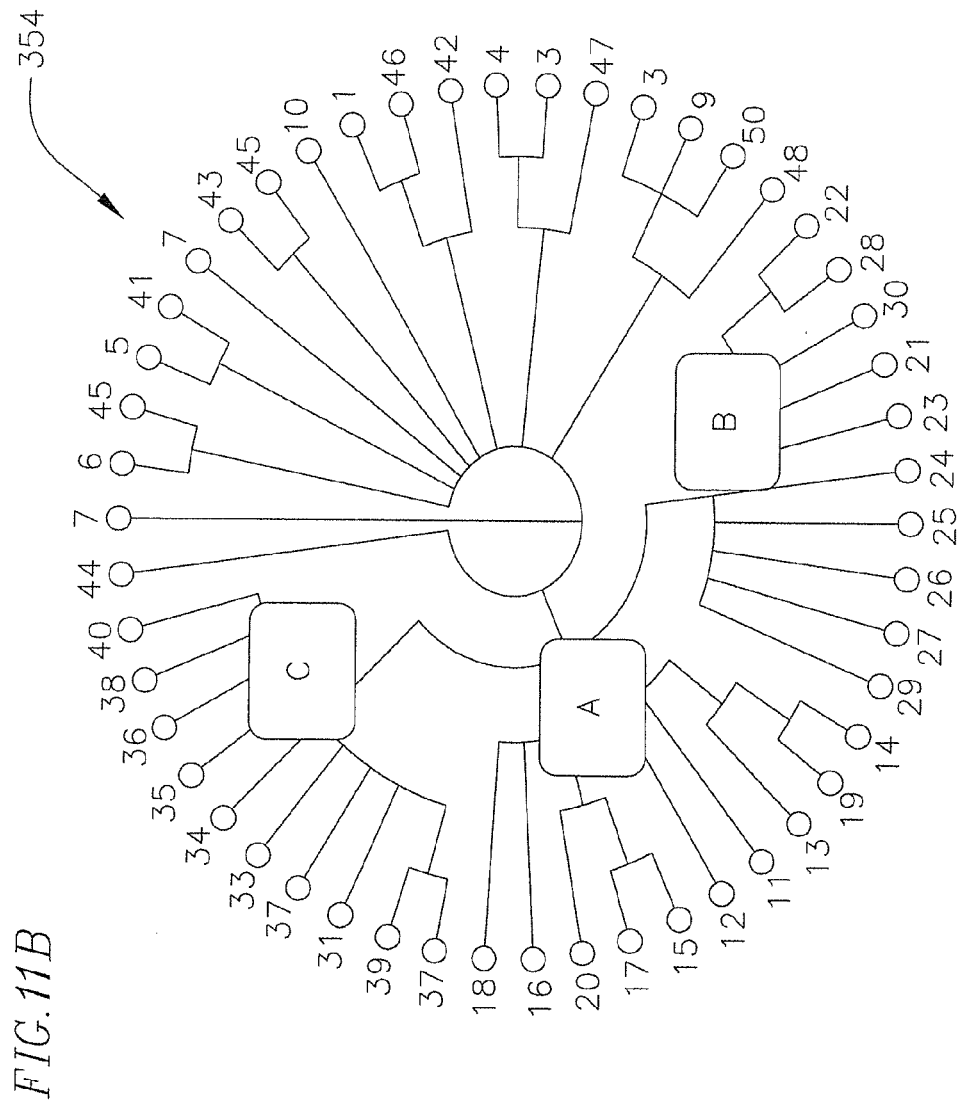

The second example illustrated in FIGS. 11A-11B show how the vHRG enables extracting a hierarchical structure from a combination of network attributes, where a network component is constrained synergistically by two separate attributes. The network also has fifty nodes along with two sets of weights, each corresponding to one of the two link attributes. Plots 350, 352 show these two link attributes constraining clusters within the network. The first attribute defines the large cluster {A, B, C}. The second attribute defines the clusters A, B, and C individually.

The proposed vHRG algorithm successfully discovers clusters at the 'finest' level and at the 'coarser' level, as shown in consensus tree 354. The individual clusters A, B, and C have been identified at the lowest level, and the larger cluster {A, B, C} has been identified at one upper level. From the fact that the individual attributes failed to identify the corresponding clusters independently, the vHRG algorithm seems to utilize the information from these attributes in a synergistic manner.

The two examples clearly demonstrate the capability of the proposed vHRG algorithm for revealing structures within a network which would not have been discovered using previous approaches. The strength comes from the approach of preserving the information from multiple relational attributes in a principled manner.

Discovering Hierarchical Community with Mixed Membership

According to one embodiment, the data processing apparatus 100 in FIG. 2, includes the MANA module 103 for discovering hierarchical community structure with mixed membership from a spatial-temporal data stream of human activities, such as communication and meeting events.

A hierarchical community is a community composed by a hierarchy of smaller communities. For example, a company may have several business units, each of which may have several departments, each of which may have several groups, and each of which may have several members. A member may have the characteristic of mixed membership, i.e., a member can belong to more than one hierarchical community. For example, in matrix organization, a member may be in one department and at the same time belong to a workforce team which is orthogonal to the fixed hierarchy of organization. Hierarchical communities may also outside of a company setting as will be appreciated by a person of skill in the art.

Data mining technologies may record human daily activities in heterogeneous and disparate data sources which may be useful to be evaluated together. For example, data may be collected in diverse disciplines and application areas such as videos, automobiles, aircrafts, satellites, biological data, intelligence analysis, finance and social science data. Such datasets are inherently multi-modal, relational, temporal, and multi-layered, as systems are interacting with humans and their environment. However, the current state-of-the-art algorithms in data mining and machine learning usually assume that data is transactional, has only one or two modes, is static (or snapshots of temporal data), or is single-layered (application domain).

As an example, automobile or aerospace companies may have layered networks of supplier information, manufacturing facilities, parts information, warranty claims, and service data. Data for each application layer is typically collected and analyzed for optimizing the application performance myopically. For example, data may be analyzed by a supplier chain management system which records and evaluates supplier and part information, manufacturing management system which schedules and allocates resources for production and the needs of equipment maintenance, warranty and quality management system which monitors warranty claims to provide early feedbacks for problems in design, manufacturing, or parts, and on-board or off-board service data recorded at the field of vehicle operations or dealerships. Current techniques for analyzing these data typically focus on one particular application layer but rarely integrate disparate data in different layers to find patterns that cannot be found in a simple source of data alone (e.g., flagging an emerging issue in warranty claims helps in alarming the existence of widespread costly repairs, but often no data analysis technique is automated to further identify the root causes of such identified issues that are potentially originated from other application layers such as part design errors or manufacturing defects).

Network analysis has proven to be a useful tool for determining and quantifying the relationships between entities in a closed system. It has been widely and successfully used in areas such as intelligence data analysis, social network analysis, Internet data processing, authorship networks, bioinformatics and medical data processing, and many others. Although some advances have been made in Network Science to better model such data, there is a need to overcome the stove-piped techniques, which deal with only one network layer, and to leverage underlying mechanisms learned in one application domain to another.

According to one embodiment, the MANA module 103 formulates layered networks for representing data from disparate data sources. Such data may be, for example, human dynamic data such as, for example, meeting events (e.g. spatial-temporal data indicating where and when physical meetings between agents/people in different groups took place) and communication events (e.g. temporal data related to emails, phone calls, and the like). The dynamic data may be obtained, for example, from one or more databases 102, 104, or acquired in real time via cellular networks 114, servers 112, and the like.

According to one embodiment, the inherently multi-modal, relational, spatial-temporal events in the dataset are represented as a coherent, multi-layered network (e.g. a dynamic meeting network and a dynamic communication network). The MANA module 103 then applies vHRG and tensor decomposition for layered network analysis to identify characteristic dimensionality and hierarchical structure hidden within the layered network. In addition to the ability to discover conventional homogeneous community, embodiments of the present invention allow discovery of relations in the mixed community of heterogeneous datasets.

According to one embodiment, the MANA module 103 invokes the vHRG algorithm to extract mixed membership communities from the dataset. For example, the dataset may include data of two agents who may meet physically or communicate via e-mail or phone calls. Thus, an agent may belong to both the physical meeting community as well as a communications community, and hence may have a mixed membership in both communities.

Different types of communications may result in different communication frequencies and durations. vHRG analyzes these communication events among agents in a coherent representation and identifies the relations of hierarchical communities among agents. For example, the vHRG may provide an optimized dendrogram representing how the different agents are connected to one another based on the different types of communications.

Tensor decomposition, which is performed according to one embodiment after mixed membership communities are extracted from the dataset via the vHRG analysis, is commonly applied to analyze multi-dimensional data as it is natural to use tensors to represent relationships between elements in a dataset. As described in Kolda et al., *Tensor Decomposition Applications*, SIAM Review 51:455 (2009), the content of which is incorporated by reference, tensor decomposition approximates high-dimensional data by factorizing it into lower dimensional components. Such reduction can reveal important attributes and features in the dataset, as well as enable the analysis of large-scale datasets. According to one embodiment, the MANA module 103 employs tensor decomposition to discover group attributes.

A tensor is an n-dimensional generalization of a matrix. Thus, a 1D tensor is a vector, a 2D tensor is a matrix, a 3D tensor is a data cube, etc. There are various methods of performing tensor decomposition. Accordingly in one embodiment, the CANDECOMP/PARAFAC (CP) method is used to decompose the high-dimensional data.

According to one embodiment, the MANA module 103 models the collected dataset using a tensor. In this regard, appropriate dimensions are selected by the user and the decomposition approximates the data by using linear combinations of lower-dimensional components (which are based on the tensor's dimensions).

Figure 12:
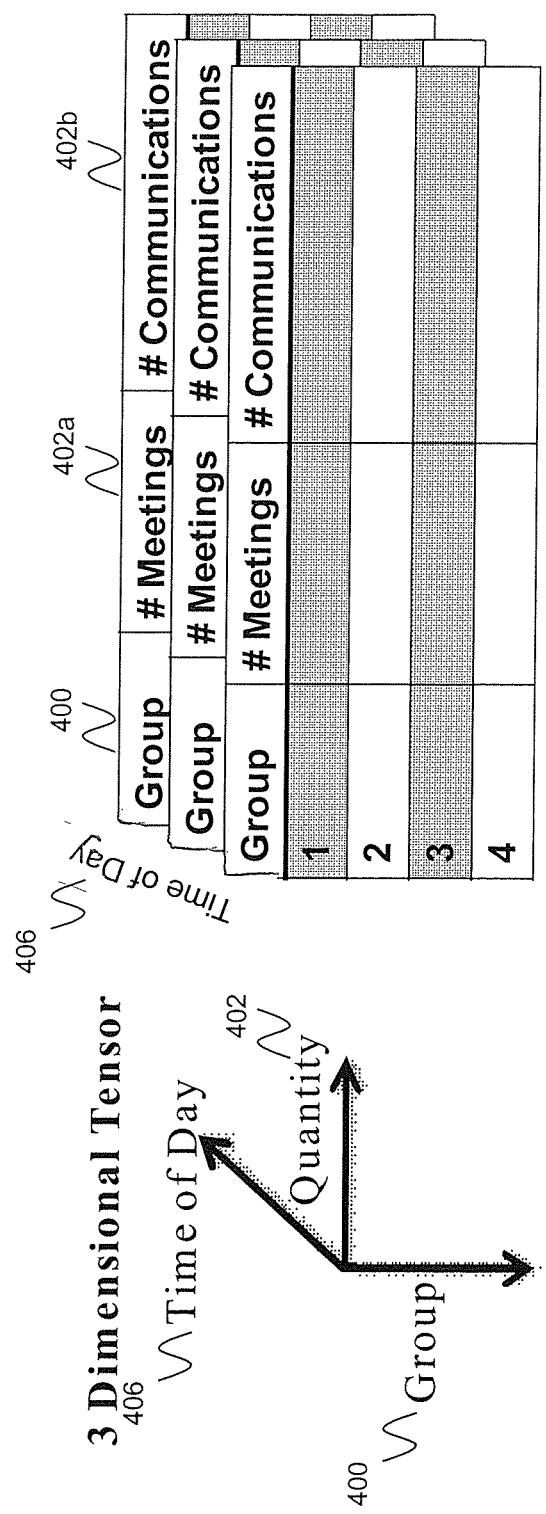
FIG. 12 is a conceptual layout diagram of a 3D tensor according to one embodiment of the invention.

FIG. 12 is a conceptual layout diagram of the dimensions of a 3D tensor. The lower-dimensional components are attributes of the dataset being modeled. In the illustrated example, clusters, or groups of individuals 400, are used as a first dimension, quantity of meetings and communications 402*a*, 402*b* (collectively 402) is used as a second dimension, and time of day 406 is used as a third dimension. A person of skill in the art should recognize that other dimensions/values may be modeled, such as, for example, a dimension may be represented based on the quantity normalized by group size or ratios of events. According to one embodiment, a subsequent decomposition step produces weighted values on each of the dimensions for each of the components as is discussed in further detail below.

As an example of the MANA functionality, it is assumed that each individual (agent) belongs to some groups and is associated with attributes that are pertinent to the groups. As an example, each individual may belong to a home group and a work group (group membership) and each group may have a different frequency in conducting physical meeting and communication events (group attributes). According to one embodiment, vHRG is used to identify groups and tensor decomposition is used to identify group attributes.

The group membership data may include: (a) the number of individuals; (b) the number of work groups; and (c) the number of home groups. Each individual may further belong to a work subgroup within the work group. The information may be tabulated into one or more tables, such as, for example, two tables with columns (agent, work_group, home_group) and (agent, work_subgroup, home_group).

Each group may also have two attributes: (a) how frequently agents meet; and (b) how frequently agents communicate with one another. The frequencies may be categorized as high, medium, or low. The attributes may also be tabulated into a table with columns (group, meeting_frequency, communication_frequency).

According to one embodiment, the databases 102, 104 further comprises information on trajectories for individuals. Such information may be obtained via any conventional mechanism known in the art, such as, for example, by tracking user movement via a GPS device installed in the user's phone, car, or the like. Information may be gathered such as information that agents start their day traveling from home to work and go back home from work at the end of a day. Whether a meeting has occurred or not may be determined based on the location of the agents as well as the time of certain events. For example, if two agents are from the same work group and their trajectories are close to each other at a specific time, they may form a working event based on their meeting frequency. Similar principles may be used to form home meeting events. However, if two agents are spatially close but belong to different home and work group, they will form unknown meeting events.

According to one embodiment, given a dataset in database 102 or 104 further comprising meeting and communication events, the MANA module 103 constructs dynamic meeting and communication networks by extracting relations stored in the database 102, 104. In the example where the dataset includes physical meeting and communication events, such as, for example, time, date, location, and/or duration of the events, and information on people participating in the events, the MANA module 103 constructs three networks: a meeting network, a communication network, and a multi-layered network with both meeting and communication events. A person of skill in the art will understand that instead of building the individual networks before building the multi-layered network, the MANA module 103 may instead build the multi-layered network directly. In the meeting network, each relation is a four tuple (id1, id2, start_time, end_time) where agent1 and agent2 identified via id1 and di2 meet from start time to end time. In the communication network, each relation is also a four tuple of (id1, id2, start_time, end_time) where agent1 and agent2 communicate from start_time to end_time.

The multi-layered network also includes a four tuple (id1, id2, v_start_time, v_end_time) where agent1 and agent2 meet and communicate from v_start_time to v_end_time. According to one embodiment, v_start_ is a vector with two elements: meeting and communication attributes, and v_end_time is also a vector with meeting and communication attributes. According to one embodiment, the normalized vector values are the weights of the link representing duration and/or frequency of the meetings and communications. If only one of the two attributes is present, the weight of the missing attribute would simply be reflected as being 0 in the multi-layered network.

Figure 13:
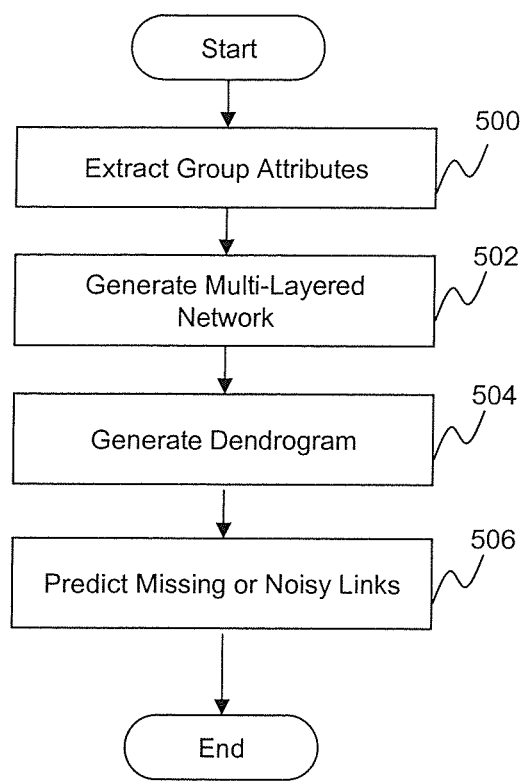
FIG. 13 is a flow diagram of a process executed by a MANA module for constructing a multi-layered network according to one embodiment of the invention.

FIG. 13 is a flow diagram of a process executed by the MANA module 103 for constructing a multi-layered network according to one embodiment of the invention. The steps of the process may be executed in the indicated order or in any other order recognized by a person of skill in the art.

In step 500, the MANA module 103 extracts group attributes and associated values from data stored in the one or more database 102, 104, or from data acquired in real time via the cellular networks 114, servers 112, and the like. According to one embodiment, the group attributes (e.g. meetings, communications, departments, organizations, etc.) may be obtained via a tensor decomposition analysis described above. According to one embodiment, the attributes are assumed to be independent.

In step 502, the MANA module 103 generates a multi-layered network based on the extracted group attributes and values. According to one embodiment, the values are normalized edge weights for each attribute, and the attributes and corresponding normalized weights are represented as a finite vector. Any one of various well known network graph generation tools may be employed to create the multi-layered network. The tool generates a link between two nodes where any one of the attributes has a normalized weight greater than 0.

In step 504, the MANA module 103 applies the vHRG algorithm for generating one or more dendrograms for the multi-layered network. The generated dendrogram allows an individual to easily see the relationship of the various agents based on a combination of the different attributes which may not be apparent from analyzing a single attribute at a time. According to one embodiment, the generated dendrogram may be output for display on a display screen of the data processing apparatus 100, or used to color the multi-layered network based on the generated dendrogram, and the colored multi-layered network may then be displayed on the display screen.

Although the MANA module 103 is described as building multi-layered networks, a person of skill in the art will recognize that the present invention is not limited to multi-layered networks, but may also be applied for constructing single-layered networks.

According to on embodiment of the invention, the MANA module 103 uses the generated dendrograms to predict missing or noisy links, as is reflected in step 506. A missing link is identified where no such link exists between two nodes, although the probability of such a link is higher than a certain threshold value which may be set by users according to their application domains, or learned from previously observed data sets. A noisy link is identified where a link exists between two nodes, although the probability of such a link is lower than a certain threshold value which may be set by users according to their application domains, or learned from previously observed data sets. For example, a network may represent N attribute sets where N={meeting, phone call, email, location, organization, department}, and the like. A missing or noisy attribute K may be identified where $K \subseteq N$ or K=N. The missing or noisy attribute K may be, for example, meetings, phone calls, etc.

According to one embodiment, the step of predicting missing attributes and links may be accomplished according to the following pseudocode:

1. Sample a set of dendrograms D at regular intervals from those generated by the Markov Chain afterwards;
2. For each pair of vertices (i,j) for which K attributes ($K \subseteq N$) are not observed in network data, calculate the mean probability $<p_{ijk}>$ for each k∈K that are linked by average over the corresponding $p_{ijk}$ in each of the sampled dendrograms D. For example, if K=(meetings, phone calls), then k is a particular attribute in K, such as meetings or phone calls.
3. Sort these pairs (i,j) and attribute k in descending order of the mean probability $<p_{ijk}>$ and declare missing attribute k for pair (i,j) if $<p_{ijk}>$ is above certain threshold.
4. For pairs in which none of attributes are observed (i.e., K=N) in network data, sort these pairs according to the geometric mean of $<p_{ijk}>$ over K and declare missing links between pair (i,j) if the average is above certain threshold.

According to one embodiment, the step of predicting noisy attributes and links may be accomplished according to the following pseudocode:

1. Sample a set of dendrograms D at regular intervals from those generated by the Markov Chain afterwards;
2. For each pair of vertices (i,j) for which K attributes ($K \subseteq N$) are observed in network data, calculate the mean probability $<p_{ijk}>$ for each k∈K that are linked by average over the corresponding $p_{ijk}$ in each of the sampled dendrograms D.
3. Sort these pairs (i,j) and attribute k in ascending order of $<p_{ijk}>$ and declare noisy attribute k for pair (i,j) if the mean probability $<p_{ijk}>$ is below certain threshold.
4. For pairs in which all attribute are observed (i.e., K=N) in network data, sort these pairs according to the geometric mean of $<p_{ijk}>$ over K and declare noisy links between pair (i j) if the average is below certain threshold.

Figure 14A:
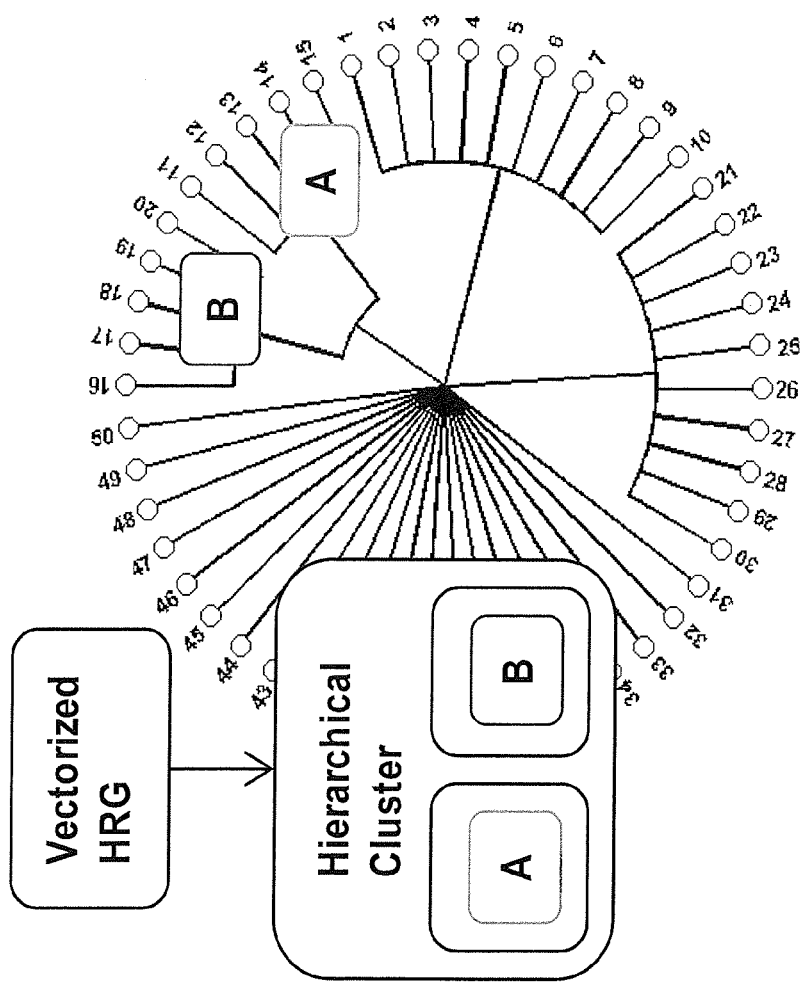
FIGS. 14A-14B are schematic diagrams of a hierarchical community structure with mixed membership that may be recovered by respectively applying a vHRG and a HRG algorithm according to one embodiment of the invention.
Figure 14B:
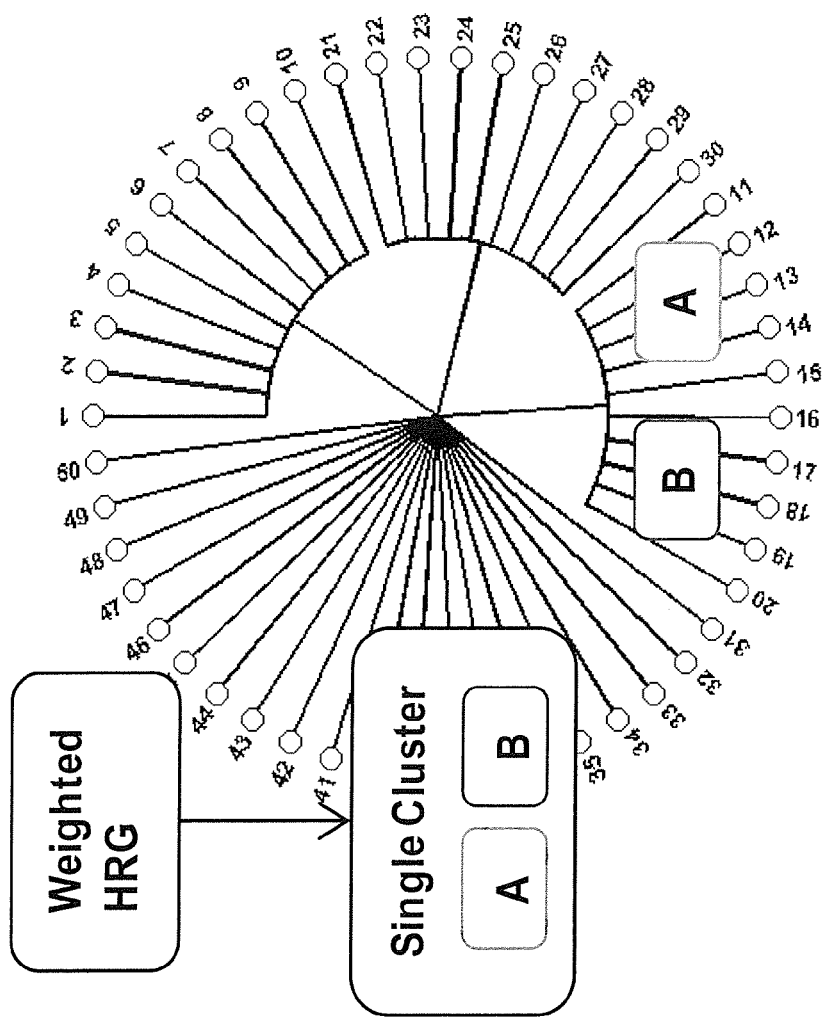

FIG. 14A is a schematic diagram of a hierarchical community structure with mixed membership that may be recovered by applying vHRG. This structure can be compared with the structure in FIG. 14B that is generated by directly applying HRG on separate single-layered networks. The mixed relations cannot be recovered in the structure in FIG. 14B, as groups A and B were merged together in FIG. 14B, whereas in FIG. 14A they remain distinct.

A person of skill in the art should recognize that the above embodiment for discovering a mixed community from multi-layered relationships within a given dataset may be used for analyzing data about different types of organizations or analyzing data collected at the border. It also has commercial applications such as analyzing product data (e.g. warranty data processing) or customer relations data (e.g. monitoring opinions), or vehicle electrification data processing).

For example, as a response to an output indicating a missing or noisy link, a user may conduct further analysis of the network data to determine whether such output is the result of incorrect data recording or other abnormal deviation from typical behavior. Another response may be to inform two agents where a particular attribute is deemed to be missing to make up for the missing attribute. For example, if two agents have not had a personal meeting for a long time (i.e. there is a missing meeting attribute between the two agents), an email may be sent to the agents prompting them to set up a meeting with one another.

Other advantages or uses of the network analysis will be apparent to a person of skill in the art. For example, data associated with social networks that update in real time may be analyzed for gathering information for advertising purposes or for criminal investigations. In such environments, people interact with one another with varying degrees of regularity. Expressing these relationships in terms of networks with weighted edges allows one to differentiate between accidental/random, casual, and regular contact between individuals. Two or more individuals making regular contact may be flagged by the data processing apparatus 100 for further investigation (e.g. background investigation).

Embodiments of the present invention is also useful to commercial applications, such as, for example, the analysis of product data including warranty data processing. In this instance, the MANA module 103 may be invoked to find correlations between part/product numbers and failures/customer complaints. This may be important when the apparent cause of a problem is two or more degrees of separation from the symptom that indicates the problem exists. For example, a number of apparently different repairs may be required across multiple lines of vehicles; one type of vehicle may overheat, while another completely different type may have trouble with its timing. Analysis of the data of the two types of vehicles modeled as a multi-layered network might show that these problems have a common cause (e.g., a faulty serpentine belt model that both vehicle lines use). Such a cause may not be immediately apparent from the individual complaints for each type of vehicle.

Although this invention has been described in certain specific embodiments, those skilled in the art will have no difficulty devising variations to the described embodiment which in no way depart from the scope and spirit of the present invention. Furthermore, to those skilled in the various arts, the invention itself herein will suggest solutions to other tasks and adaptations for other applications. It is the applicants intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

What is claimed is:

1. A computer implemented method for modeling and analyzing relational data represented in a network including a plurality of nodes and a plurality of connections between the nodes, the method comprising:
    assigning a vector of at least two attributes to a connection between two nodes in the network, each of the at least two attributes having a corresponding weight, each of the corresponding weights being greater than 0 and less than or equal to 1;
    generating a set of possible dendrograms for the network;
    determining a first likelihood of each dendrogram in the set, wherein the first likelihood is based on the weight of a first attribute of the vector of at least two attributes of the connection;
    determining a second likelihood of each dendrogram of the set, wherein the second likelihood is based on the weight of a second attribute of the vector of at least two attributes of the connection, the second attribute being different from the first attribute;
    selecting one of the dendrograms from the set based on the product of the first likelihood and the second likelihood; and
    outputting the selected dendrogram via an output device,
    wherein there is no more than one connection between any two nodes of the nodes, and
    wherein a first weight of a first connection of the connections has a value different from a second weight of a second connection of the connections.

2. The method of claim 1, wherein the weight is reflective of a strength of the connection between the two nodes in the network.

3. The method of claim 1, wherein the first attribute is a dynamic attribute configured to change over time.

4. The method of claim 3, wherein the weight is a function of time.

5. The method of claim 1 further comprising:
    extracting the vector of attributes and the weights for the attributes from a dataset; and
    generating the network based on the plurality of attributes.

6. The method of claim 5 further comprising:
    identifying a missing or noisy attribute in the connection between the two nodes.

7. The method of claim 5 further comprising:
  detecting that a connection is missing between two nodes in the generated network, or that the connection between two nodes in the generated network is a noisy connection.

8. The method of claim 5 wherein the selected dendrogram provides a hierarchical community structure denoting connectivity in the generated network.

9. The method of claim 5, wherein the attributes are extracted via tensor decomposition.

10. A data processing apparatus adapted for modeling and analyzing relational data represented in a network including plurality of nodes and a plurality of connections between the nodes, the data processing apparatus comprising:
  a processor; and
  a memory operably coupled to the processor and having program instructions stored therein, the processor being operable to execute the program instructions, the program instructions including:
    assigning a vector of at least two attributes to a connection between two nodes in the network, each of the at least two attributes having a corresponding weight, each of the corresponding weights being greater than 0 and less than or equal to 1;
    generating a set of possible dendrograms for the network;
    determining a first likelihood of each dendrogram in the set, wherein the first likelihood is based on the weight of a first attribute of the vector of at least two attributes of the connection;
    determining a second likelihood of each dendrogram of the set, wherein the second likelihood is based on the weight of a second attribute of the vector of at least two attributes of the connection, the second attribute being different from the first attribute;
    selecting one of the dendrograms from the set based on the product of the first likelihood and the second likelihood; and
    outputting the selected dendrogram via an output device,
  wherein there is no more than one connection between any two nodes of the nodes, and
  wherein a first weight of a first connection of the connections has a value different from a second weight of a second connection of the connections.

11. The data processing apparatus of claim 10, wherein the weight is reflective of a strength of the connection between the two nodes in the network.

12. The data processing apparatus of claim 10, wherein the first attribute is a dynamic attribute changing over time.

13. The data processing apparatus of claim 12, wherein the weight is a function of time.

14. The data processing apparatus of claim 10, wherein the program instructions further comprise:
  extracting the vector of attributes and the weights for the attributes from a dataset; and
  generating the network based on the plurality of attributes.

15. The data processing apparatus of claim 14, wherein the program instructions further comprise:
  identifying a missing or noisy attribute in the single connection between the two nodes.

16. The data processing apparatus of claim 14, wherein the program instructions further comprise:
  detecting that a connection is missing between two nodes in the generated network, or that the connection between two nodes in the generated network is a noisy connection.

17. The data processing apparatus of claim 10, wherein the selected dendrogram provides a hierarchical community structure denoting connectivity in the generated network.

18. A non-transitory computer readable medium embodying program instructions for execution by a data processing apparatus, the program instructions adapting a data processing apparatus for modeling and analyzing relational data represented in a network including a plurality of nodes and a plurality of connections between the nodes, the program instructions comprising:
  assigning a vector of at least two attributes to at least one connection of the plurality of connections, each of the at least two attributes having a corresponding weight, each of the corresponding weights being greater than 0 and less than or equal to 1;
  generating a set of possible dendrograms for the network;
  determining a first likelihood of each dendrogram in the set, wherein the first likelihood is based on the weight of a first attribute of the vector of at least two attributes of the connection;
  determining a second likelihood of each dendrogram of the set, wherein the second likelihood is based on the weight of a second attribute of the vector of at least two attributes of the connection, the second attribute being different from the first attribute;
  selecting one of the dendrograms from the set based on the product of the first likelihood and the second likelihood; and
  outputting the selected dendrogram via an output device,
  wherein there is no more than one connection between any two nodes of the nodes, and
  wherein a first weight of a first connection of the connections has a value different from a second weight of a second connection of the connections.

* * * * *